(12) United States Patent
Sibson

(10) Patent No.: US 6,348,313 B1
(45) Date of Patent: Feb. 19, 2002

(54) SEQUENCING OF NUCLEIC ACIDS

(75) Inventor: David Ross Sibson, Amersham (GB)

(73) Assignee: Medical Research Council (GB)

( * ) Notice: Subject to any disclaimer, the term of this patent is extended or adjusted under 35 U.S.C. 154(b) by 0 days.

(21) Appl. No.: 08/676,342

(22) PCT Filed: Jan. 20, 1995

(86) PCT No.: PCT/GB95/00109

§ 371 Date: Jul. 19, 1996

§ 102(e) Date: Jul. 19, 1996

(87) PCT Pub. No.: WO95/20053

PCT Pub. Date: Jul. 27, 1995

(30) Foreign Application Priority Data

Jan. 21, 1994 (GB) .......................................... 9401200

(51) Int. Cl.[7] ................................................ C12Q 1/68
(52) U.S. Cl. ............................................ 435/6; 436/94
(58) Field of Search ............................... 435/6; 436/94; 536/24.1, 24.2, 22.1; 935/77, 78

(56) References Cited

U.S. PATENT DOCUMENTS 4,962,037 A  * 10/1990 Jett et al. ....................... 435/6
5,552,278 A  *  9/1996 Brenner ......................... 435/6
5,599,675 A  *  2/1997 Brenner ......................... 435/6

OTHER PUBLICATIONS

Mormenco et. al. Gene 61:21–30 (1987).*
Promega catalog 1993/1994 pp. 1–3 and 136.*
Szybalski Gene 40:169–173 (1985).*
Ausubel et.al ed.s Shoa Protoclos in Molecular Biology John Wiley and Sons (1989) pp. 87–98 and 113–121.*

* cited by examiner

*Primary Examiner*—Ardin H. Marschel
(74) *Attorney, Agent, or Firm*—Millen, White, Zelano & Branigan, P.C.

(57) ABSTRACT

The present invention provides a method of sequencing a nucleic acid, comprising either sequentially removing bases from the sequence of the nucleic acid a predetermined number at a time, with the product remaining from each step of predetermined base removal being ligated to a labeled adapter specific for said bases and including oligonucleotide sequence, or hybridizing a primer to the nucleic acid to be sequenced and sequentially extending said primer a predetermined number of bases at a time, said added base(s) being complementary to base(s) in the nucleic acid being sequenced, and each of said base addition steps being achieved by the use of a labeled adaptor specific for said bases and including oligonucleotide sequence containing said predetermined base(s); in either case, the label of said labeled adaptor being specific for its respective predetermined base(s).

13 Claims, 7 Drawing Sheets

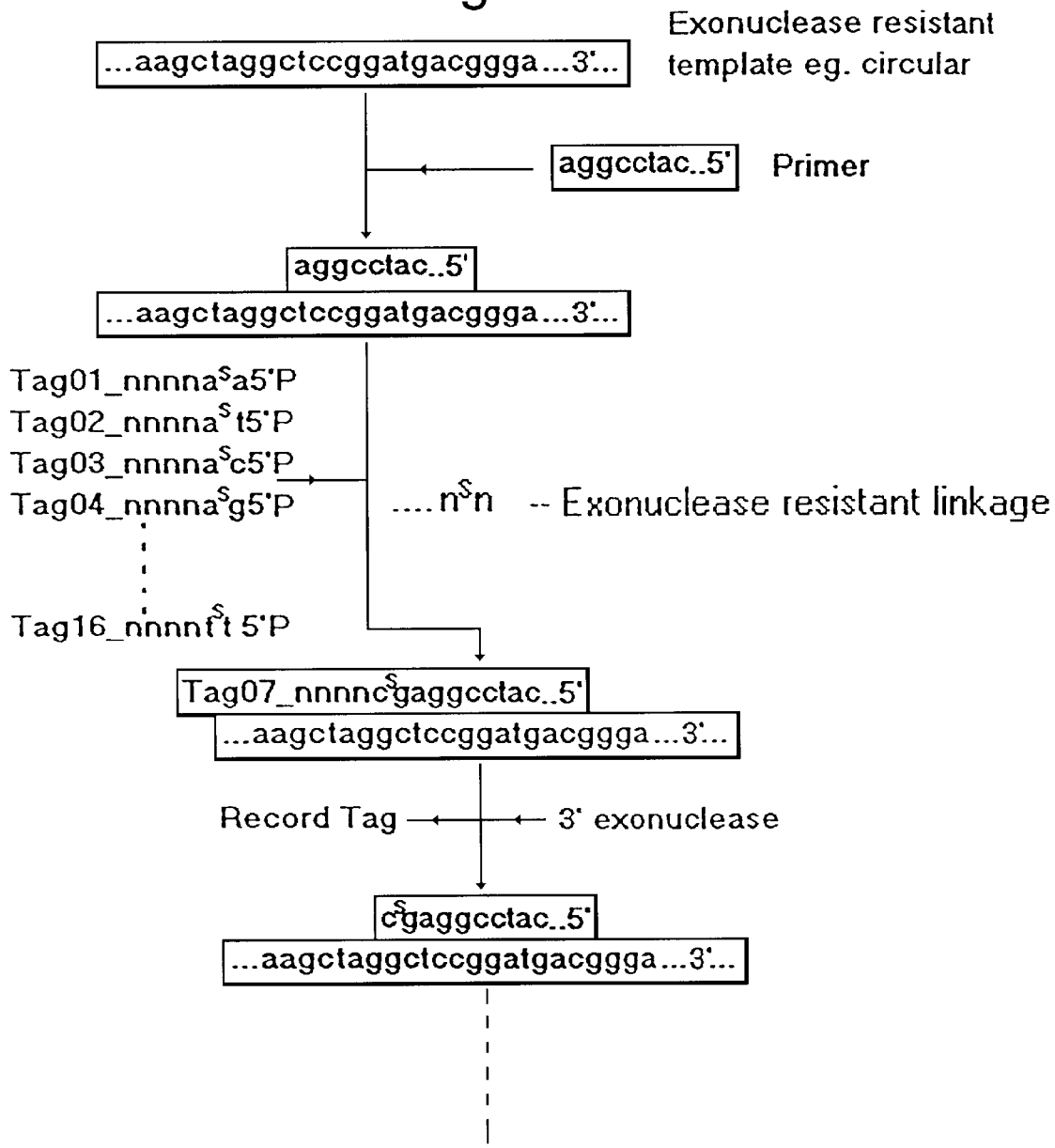

SEQUENCING OF NUCLEIC ACIDS

Figure 1A:
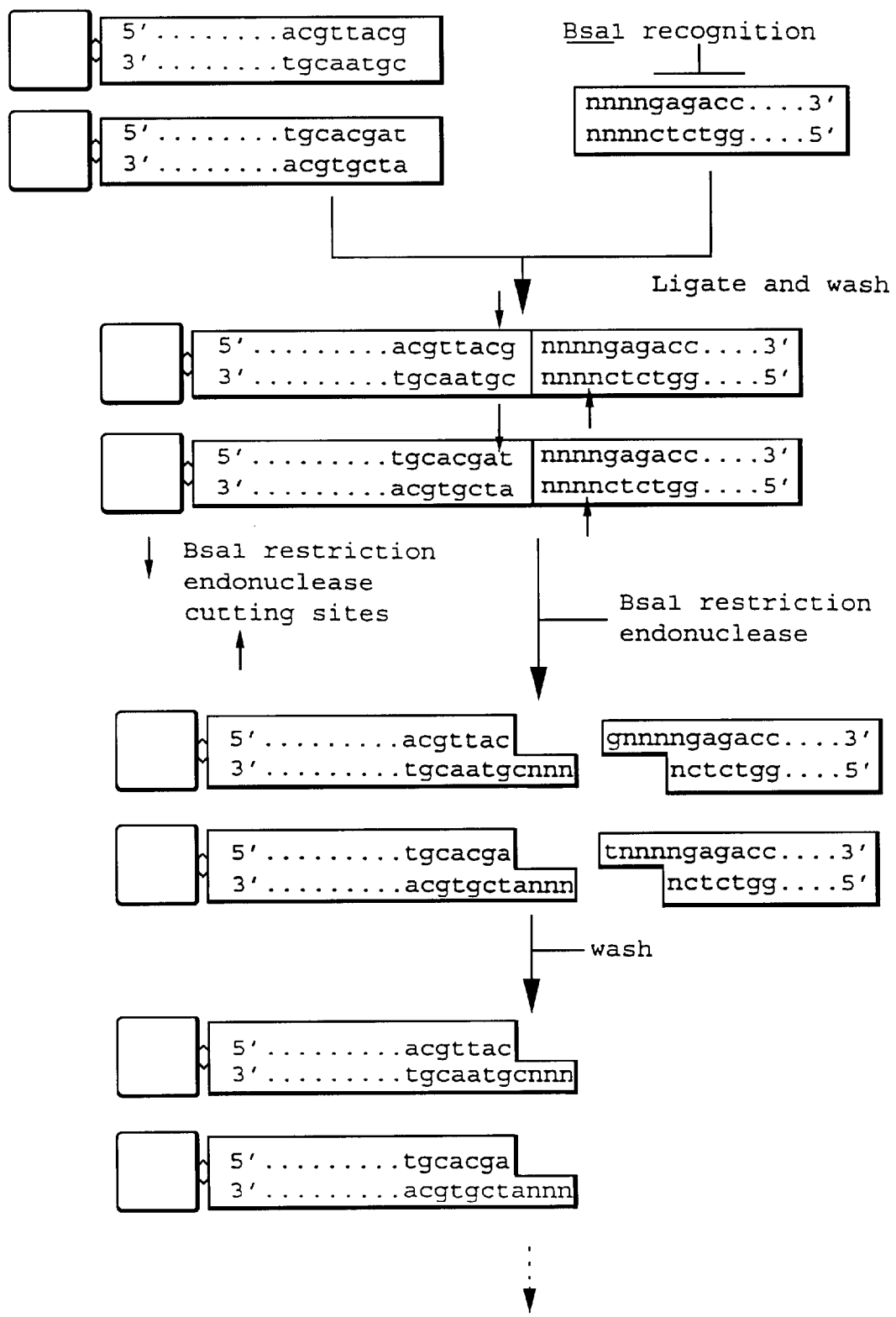

This invention relates to new techniques for the sequencing of nucleic acids based upon a general approach in which labelled adaptor molecules are employed. The invention facilitates the large scale analysis of populations of nucleic acids, for example populations of sequences as produced in the Human Genome Project (HGP). Its applicability is, of course, not limited to HGP or its like.

Conventional analysis of nucleic acid sequences has hitherto depended largely on the base specific fragmentation of the original nucleic acid sample into two or more parts differing in size by one or more bases. Sequencing is effected by separation of the resultant fragments followed by their analysis.

In relatively low throughput sequence analysis of RNA, base specific fragmentation has been effected by ribonucleases with base specific activities, followed by thin layer chromatographic separation of the products. Higher throughput sequence analysis, especially of DNA, generates the fragments to be analyzed by base specific chemical cleavage (Maxam, A. M. and Gilbert, W Proc. Natl. Acad Sci. 74 p560 (1977) or by terminating, in a base specific manner, synthesis catalysed by a suitable nucleic acid polymerase (Sanger, F., Nicklen, S and Coulson, A. R., Proc. Natl. Acad Sci. 74 p5463 (1977)). Separation of the resultant fragments is achieved by denaturing gel electrophoresis through ultra thin slabs or capillaries containing a suitable polymer like polyacrylamide. This can resolve of the order of about a thousand bases per suitably prepared sample at a resolution of one base, and can handle tens of samples simultaneously. Detection (Smith, L., M. and Youvan, D., C. Biotechnolgy 7 p576–580 (1989)) (Yang, M., M., and Youvan, D., C., Biotechnology 7 p576–580 (1989)) has been direct or indirect through radioactive, chemiluminescent or fluorescent labelling or by stable isotopes (Human Genome 1991–1992 Program Report p18 and p22 U.S. department of Energy 1992)).

There is a great deal of interest in achieving greater rates of sequencing at reduced cost. It will then be feasible to analyze completely the genomes of organisms, in particular those of higher eucaryotes which are commonly over 3,000,000,000 bases in size per haploid genome. Furthermore, methods which are suitable for such analysis will also make it possible to perform high resolution linkage analysis on many individuals in a population. This will be important for identifying the phenotypes, especially common diseases, associated with genes, and to trace gene flow in humans. Analyzing the expressed sequences in a population of cDNAs or mRNAs would also become possible. It would also be possible repeatedly to sequence the same region or multiple regions from many different individuals for the purposes of comparisons related to for example diagnosis.

Very high throughput methods of sequence analysis are therefore being investigated (desirably one or more orders of magnitude greater than achievable with current, conventional, commercially available sequencing apparatus, such as the ABI 373 DNA sequencing System which can read not more than 1000 bases a day from 72 samples). Scanning tunnelling electron microscopy can directly visualise the bases in individual molecules. Lasers might also be usable to sort individual molecules, which can then be analyzed by degrading them from one end, a base at a time (Harding, J. D. and Keller, R. A. Trends in Biotech 10 p55–58 (1992).

However, there is a further problem when it is desired to conduct sequence analysis at a rate adequate for analyzing whole genomes or adequate for comparing many selected sequences from many individuals (for example, when using family studies to identify the locus of an inherited trait), namely many samples need to be simultaneously analyzed. This is currently being approached through sequencing by hybridisation.

There are two formats for sequencing analysis by hybridisation. One format (Drmanac, R., et al Genomics 4 p114–128 (1989) and Stretzoska, Z., et al Proc. Natl. Acad. Sci USA 88 p10, 089–10,093 (1991)) immobilises many samples (perhaps numbering hundreds of thousands) separately on a large array. The array is probed in turn by each of many different labelled oligonucleotides of known sequence. Identification of samples which have hybridised to each of the probes, indicates those which have complementary sequences to the probe. Use of multiple probes covering all possible sequences allows the complete sequences of the samples to be assembled. This method is, however, limited by the requirement for oligonucleotides of at least 5 bases to achieve specific hybridisation, which in turn dictates that large numbers of probes ($4^n$ where n is the length of the oligonucleotide) are required to cover all possible sequence combinations.

The alternative format (Fodor, S. et al Nature 364 P555–556 (1993), Kharpko, K., R., et al DNA Sequence 1 p375–388 (1991), Southern, E., M., Maskos, U., and Elder, J., K. Genomics 13 p1008–1017 (1992)) requires many thousands of different oligonucleotides, each with different known sequence covering together all possibilities, to be immobilised on a suitable array. Probing the array with a labelled nucleic acid sample whose sequence is to be analyzed identifies the oligonucleotides which share homology with the sample. This is usually achieved through synthesis of the oligonucleotides in situ with masking, for example by a lithograph, of those not requiring the specific base being added at any given time. The sample is labelled and hybridised to the array. The positions of hybridisation indicate where sequence homologies are shared between the sample and the detected oligonucleotides. Therefore the sequences of the sample can be deduced from those of the detected oligonucleotides.

In either format for sequencing by hybridisation, it is difficult in practice to synthesise oligonucleotides of adequate length. When oligonucleotides are immobilised and probed with sample, in practice only short oligonucleotides can be synthesised on arrays of necessarily limited size.

Alternatively, and as mentioned above, when oligonucleotides are synthesised independently to probe an array of samples, the number required to cover all sequence possibilities is $4^n$, where n is the length of each oligonucleotide. It is logistically challenging both to produce and to use the number required to accurately detect all possible sequences. For example, the number required to make all possible 5 mers is 1024.

The length of the oligonucleotides determines their fidelity of hybridisation, and also the ease with which full sequence can be assembled from the component oligonucleotide sequences. In each case longer oligonucleotides are better. Greater fidelity of hybridisation is achieved the longer the oligonucleotides used since more stringent washing can be performed when the oligonucleotides are as long as possible. When full length sequence is being assembled from overlapping component sequences, the longer the component sequences the fewer possible "solutions" that there are likely to be.

A further problem associated with the sequencing by hybridisation format where probe oligonucleotides are immobilised is that as the size of the target increases the proportion of any given region within that target decreases. This reduces signal to noise, and therefore has the effect of limiting the size of target, which can be analyzed.

Hybridisation used alone, is in general not a good means of analyzing sequences because not all oligonucleotides hybridise with equal efficiency or specificity under a given range of conditions. There are therefore associated interpretational and/or practical difficulties.

The possibility for enzymatic sequencing in situ on arrays of immobilised samples has also been reported (Rosenthal, A. and Brenner, S. 1993 Meeting on Genome maping and sequencing page 222 Cold Spring Harbor Laboratory Press (1993). Each base is labelled differently and added to the samples such that extension is terminated at a given base. The number and type of added bases is recorded for each sample. The block to extension is removed so that the exercise can be repeated for the next base to be so tested. Cycles of testing each base in turn produces complete sequence for each sample. This method suffers the difficulties of distinguishing the number of members in a homopolymeric sequence and that different molecules within a given sample become out of phase with each other with respect to the position of the bases being analyzed.

WO 94/01582 discloses a process for the categorization of nucleic acid sequences using a population of adaptor molecules which include predetermined nucleotide bases, categorization of the nucleic acid sequences being achieved by linkage between them and the adaptor molecules and selection of the resulting ink sequences in a base-specific manner. The adaptors in question are preferably short double stranded oligonucleotides which have an extending strand to allow base-specific ligation to nucleic acid sequences which have been produced by cleavage involving a nuclease in which the recognition and cleavage sites are displaced from each other.

A method of sequentially determining the order of bases one or more bases at a time on many samples simultaneously would be attractive if available because it could be automated, would require few reagents and might allow of the order of tens of bases to be determined which would facilitate assembly of full length sequence. Each sequence of 17 bases, for example, excepting the repetitive elements which comprises a low complexity special case, is likely to be unique in the human genome. Producing overlapping sequences of 17 or more bases from the human would therefore facilitate assembly of the unique human sequences. In order for such a process to be successful it is necessary to determine the order of bases on all samples one or more at a time without allowing molecules within any of the samples to become out of phase during the process. This is achieved for the first time by the present invention.

The present invention is based upon the use of specific adaptors including oligonucleotide sequence comprising one or more predetermined bases. In some embodiments of the invention, use is also made of restriction enducleases having a recognition site displaced from the cleavage site. All embodiments depend, however, upon the use of the aforementioned adaptors.

Thus, the present invention provides a method of sequencing a nucleic acid, comprising either sequentially removing bases from the sequence of the nucleic acid a predetermined number at a time, with the product remaining from each step of predetermined base removal being ligated to a labelled adapter specific for said bases and including oligonucleotide sequence, or hybridising a primer to the nucleic acid to be sequenced and sequentially extending said primer a predetermined number of bases at a time, said added base(s) being complementary to base(s) in the nucleic acid being sequenced, and each of said base addition steps being achieved by the use of a labelled adaptor specific for said bases and including oligonucleotide sequence containing said predetermined base(s); in either case, the label of said labelled adaptor being specific for its respective predetermined base(s).

The predetermined base removal embodiments are best suited to double stranded nucleic acids, and the technique can use nucleases as described herein. Of course, any other appropriate method of base specific cleavage can be used if desired.

Thus, a further aspect of the invention is a method of sequencing a population of double stranded nucleic acids, comprising:

(a) ligating to said nucleic acids adaptors which include double stranded oligonucleotide sequence which incorporates a predetermined nuclease recognition sequence for a nuclease whose recognition site is displaced from its cleavage site, said displacement being such as to create, as a result of said ligation, cleavage sites in the resulting ligation products which, upon cleavage thereat, result in removal of a base or bases from one strand of said nucleic acids;

(b) cleaving ligation products from (a) with said nuclease to produce double stranded products of unequal strand length;

(c) subjecting said products from (b) to ligation with a population of adaptors which include double stranded oligonucleotide sequence having extending single strands wherein said population of adaptors includes molecules having in their extending single strands at least a predetermined subset of all possible permutations of a base or bases constituting a predetermined number of bases, and wherein each permutation is provided with a respective unique and detectable label, each adaptor in said population having a nuclease recognition sequence for a nuclease whose recognition site is displaced from its cleavage site, said displacement being such as to create, as a result of the ligation of this step (c), upon cleavage thereat, result in removal of a base or bases from one strand of said products from (b);

(d) separating the ligation products from (c);

(e) cleaving the separated ligation products from (c) with the nuclease of (c) to produce a population of fragments carrying the recognition site of the nuclease of (c);

(f) either analyzing the labels carried by ligation products separated in (d), or analyzing the labels carried by fragments from (e); and (g) repeating steps (c) to (f) as often as necessary to determine the desired sequence, but with the final repeat optionally omitting step (e).

Preferably, in (c) above, all possible base permutations would have a unique label, but it is sufficient to label a subset of the permutations as long as analysis is not wished to proceed at a rate greater than determined by the proportion of the permutations which are labelled. For example, a 4 base extension has 256 permutations. If 16 "colours" were available as labels, all of the permutations of possible bases at 2 of the 4 bases in the extension could be labelled and deleted independently. Of course, only "bases worth" of information would be determined.

As will be clear from the description hereinafter, it will be appreciated that the "predetermined number of bases"

referred to in (c) above is the base or bases which are being monitored for sequencing purposes. The number of such bases can be one or more.

Although the above process is defined by reference to nucleases and nuclease cleavage and recognition sites, other means of achieving the same effect of stepwise base removal are expressly envisaged by the invention and not excluded. Obviously, the use of particular restriction endonucleases (see below) is very convenient and preferred but is not absolutely essential.

Preferably, the above process is preceded by treatment of the population of nucleic acids with the nuclease(s) to be used later in the process.

Other aspects of the invention are the use of the nuclease having a recognition site displaced from its cleavage site in the sequencing of nucleic acid, and a kit for sequencing nucleic acid which comprises at least one nuclease having its recognition site displaced from its cleavage site and/or a population of double stranded oligonucleotides in which the strands are of unequal length with one or more predetermined bases in the extending strand and with the double stranded portion including a recognition site for a nuclease having its recognition site displaced from its cleavage site.

Preferably, there is a recognition site for more than one nuclease because the choice can be exercised as to which nuclease is to be used for base specific removal. This would be an advantage, for example, when there is already a site for one nuclease in the sample being sequenced, but not the other. It is practical to fit more than one recognition site in the oligonucleotides or adaptors provided the sites do not overlap. Alternatively, a plurality of sites works if the sequences of the recognition sites either are partially the same in a way which will accommodate partial overlap without either recognition site being altered. The same "types" of cut ends must also be generated by the enzymes. For example, the recognition site for a nuclease which produces a 3' overhang would preclude the simultaneous use of a recognition site for a nuclease which produces a 5' overhang.

The predetermined base addition embodiments of the invention are best suited to sequencing a single stranded nucleic acid provided with at least some known sequence. Accordingly, another aspect of the present invention is a process for sequencing single stranded nucleic acid having or being provided with at least some known sequence, comprising:

(a) annealing an oligonucleotide primer to said known sequence immediately adjacent to the unknown sequence to be determined in said nucleic acid;

(b) subjecting the end of said oligonucleotide immediately adjacent to the unknown sequence to ligation with a population of labelled adaptors having oligonucleotide sequence including all possible permutations of a predetermined number of bases positioned at the end thereof which is so-ligated, the adaptors of said population being employed simultaneously, in preselected groups, or one by one, as desired;

(c) detecting the specific adaptor from said population which was ligated in (b);

(d) removing all of said specific ligated adaptor except for said one or more predetermined bases thereby to extend the double stranded region of the resulting product; and (e) repeating steps (b) to (d) to the necessary extent to determine the unknown sequence, but with the final repeat optionally omitting step (d).

Since all processes in accordance with the present invention require the use of labelled adaptor molecules which are preferably, but not essentially, entirely constituted by an oligonucleotide, it is important to note the nature of the label in question is not significant to the invention. Any workable means of detecting with specificity particular adaptors, whether in ligated condition or not, and hence the particular predetermined bases they carry, is adequate for the purposes of the present invention. Useable labels include those known to the skilled person, for example, radioactive isotopes, stable isotopes, homologous or similar sequences, dyes, fluorescent compounds, enzymes, biotin, carbohydrates. The term "label" is to be broadly construed to cover an entity which can be detected by any means without undue interference with the sequencing process.

This invention will now be further described in detail with reference to the various categories of embodiment discussed above.

Turning first to the aspect of the invention which is constituted by the predetermined base removal process, it will be noted that this process takes advantage of the certain category of restriction endonucleases selectively to degrade all samples simultaneously by a predetermined number of bases from one end, and to record the bases at each modified end either just before or just after degradation. Cyclical repetition of the process generates lengthy sequence information of the order of tens of bases from the sample ends.

Nucleases which can be employed in this process include restriction endonucleases the cleavage sites of which are asymmetrically spaced across the two strands of a double stranded substrate, and the specificity of which is not affected by the nature of the bases adjacent to a cleavage site. Type II restriction endonucleases of these types together cover a wide range of specificities, are readily available, and are highly specific and efficient in their action (Review: Roberts, R. J. Nucl. Acids res. 18, 1990, p2331–2365).

TABLE 1

Enzymes whose cleavage site is outside of their recognition site and are therefore suitable for use in sequencing by base removal.

| | |
|---|---|
| Alwl | GGATC(4/5) |
| Bbsl | GAAGAC(2/6) |
| Bbvl | GCAGC(8/12) |
| Bce83l | CTTGAG(16/14) |
| Bcefl | ACGGC(12/13) |
| Bcgl | (10/12)GCAN6TCG(12/10) |
| Bpml | CTGGAG(16/14) |
| Bsal | GGTCTC(1/5) |
| Bsgl | GTGCAG(16/14) |
| BsmAl | GTCTC(1/5) |
| BspMl | ACCTGC(4/8) |
| Earl | CTCTTC(1/4) |
| Eco57l | CTGAAG(16/14) |
| Esp3l | CGTCTC(1/5) |
| Faul | CCCGC(4/6) |
| Fokl | GGATG(9/13) |
| Hgal | GACGC(5/10) |
| Hphl | GGTGA(8/7) |
| Mboll | GAAGA(8/7) |
| Mmel | TCCRAC(20/18) |
| Mnll | CCTC(7/6) |
| Plel | GAGTC(4/5) |
| RleAl | CCCACA(12/9) |
| Sapl | GCTCTTC(1/4) |
| SfaNl | GCATC(5/9) |
| Taqll-1 | GACCGA(11/9) |
| Taqll-2 | CACCCA(11/9) |
| Tth111ll | CAARCA(11/9) |

Thus, the predetermined base removal process makes use of base specific cleavage towards the end of samples to be analysed. Of course, it is possible (and this is generally likely to be the case) that the samples being analysed will include sequences having a nuclease cleavage site internally. Such samples must be pre-prepared such that the base specific cleavage employed does not occur internally as well as at the desired end. One means of achieving this is to pretreat sample with the appropriate nuclease or nucleases such that the resulting fragments cannot thereafter be cleaved by such nuclease(s). In effect, sequence analysis is then confined to the ends of the resulting fragments. If desired, a known pattern of pre-cleavage involving selected nucleases can be employed before the performance of the present process, using not only nuclease enzymes subsequently to be employed in the process but other nucleases in addition.

Additionally, nucleic acid samples to be sequenced can be prepared so that they can be simultaneously treated by the process and analysed without interference between individual nucleic acids. One means of achieving this is to have each nucleic acid in a separate reaction vessel. The invention, however, readily lends itself to preferred simultaneous processing and analysis of many samples in the same reaction vessel, with nucleic acids distinguishable in that vessel by the use of independent immobilisation.

Preferably ligation reactions used in the processes of the present invention are catalyzed by DNA ligase, which enzyme is, of course, readily available and easy to use.

Figure 1B:
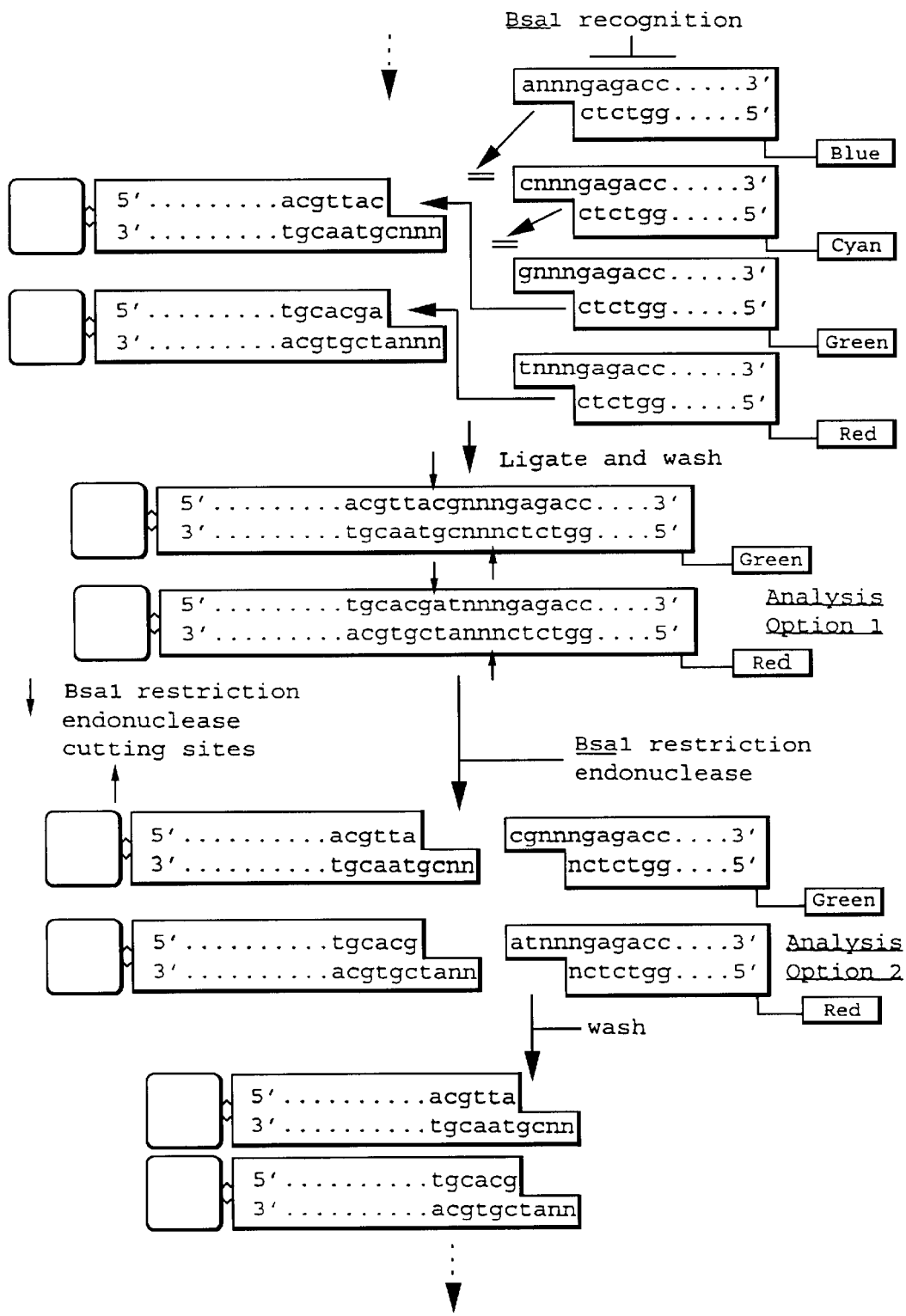
Figure 1C:
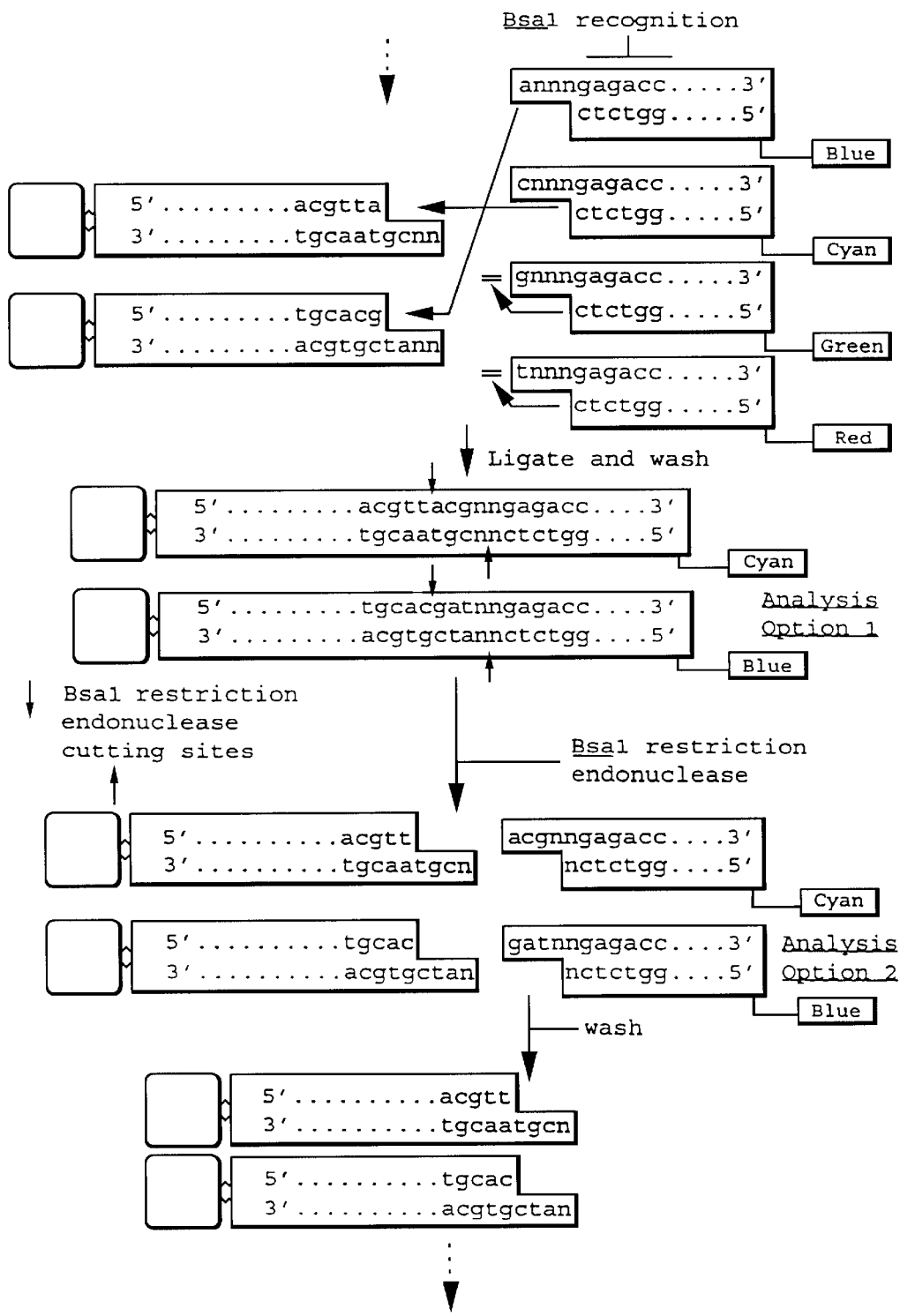

The general scheme of the predetermined base addition method is illustrated in the attached FIG. 1. In the scheme shown in FIG. 1, for purposes of illustration a single restriction endonuclease is employed, namely Bsa I. However, the predetermined base removal aspects of the present invention are not limited to the use of a single predetermined nuclease. If desired, a predetermined pattern of use of different nucleases can be employed at different stages during the sequencing operation.

In the scheme shown in the attached FIG. 1, fragments to be analysed are first created by Bsa I, which is also utilized for the stepwise base specific analysis of the ends. This avoids the possibility of the enzyme cutting internally during analysis until such time as the sequence is "used up" as a result of stepwise degradation.

In a large nucleic acid, on average the fragments can be classified into three types dependent on whether (and how) or not they retain the Bsa1 recognition site. One type will have Bsa1 at neither of its ends. One type will have Bsa1 recognition sequence at one of its ends, one type will have Bsa1 recognition sequence at both of its ends. On average they will be in the proportion 1:2:1, respectively. In this case analysis is confined to those fragments which completely lack Bsa1 recognition sequence. There are many ways that one skilled in the art can select for the required fragments and instances of these can be found in the Examples hereinafter. Additionally, there are ways that one skilled in the art can select for the removal of Bsa1 recognition sequence from ends where such sequence does occur. One such method would be to ligate to Bsa1 cut DNA, in the presence of active Bsa1, adaptors with a Bsa1 recognition sequence whose use will result in removal of bases from the nucleic acid sample being sequenced. Once an adaptor has ligated there are two possible outcomes at each cleavage which follows. Either the Bsa1 site in the fragment is used, in which case part of the adaptor is cleaved off. Alternatively, the Bsa1 site of the adaptor is utilised in which case bases are removed from the sample. Cycles of addition and cleavage will ensue. Eventually by chance the Bsa1 site of the sample will be removed and further cleavages will be from the sample. Suitable titration will determine the level of treatment required to give a population sufficiently depleted in Bsa1, but not overly reduced in average size by digestion from the adaptor. This is in fact, a general way of exposing internal sequences to the sequencing process. Other such methods are known (for example treatment with DNAse 1 in the presence of manganese$^{2+}$, treatment with Ba131 or by random shearing (Sambrook, J., Fritsch, E. G. and Maniatis, T. ed (1989). "Molecule Cloning". Cold Spring Harbor Laboratory Press, New York)).

Importantly, in the scheme shown in FIG. 1, two general types of adaptor molecule are utilized.

The first type of adaptor molecule, shown in FIG. 1 as an oligonucleotide as such, contains base sequence which includes the recognition site for Bsa I e.g., nucleotides 1–10 of 5–8 and its complement. The location of the Bsa I recognition site within the adaptor is such that upon ligation with blunt ended nucleic acid sequences of interest and subsequent cleavage by Bsa I, a selected number of bases will be removed from the end of the nucleic acid being analyzed, thus exposing complementary bases for analysis. This requires that the number of bases in the adaptor between the recognition site and the point of cleavage is fewer, by the number of bases to be removed from the nucleic acid being sequenced (the predetermined number of bases), than the maximum cutting distance of the enzyme Bsa I from its recognition site.

Of critical importance for the continuing cyclical nature of the process is that whichever endonuclease is employed, it should not cut to leave a blunt end. The overhang or extending strand which remains can be either 3' or 5' depending upon the nature of the cleavage which is produced.

In FIG. 1 it can be seen from the first stage that the adaptor molecules used have a recognition site for Bsa I which is situated four bases from the oligonucleotide sequence end which is to be ligated to the nucleic acid to be sequenced. Since Bsa I cuts five bases away from its recognition site to leave a four base 5' overhang, upon cleavage one predetermined base is therefore effectively removed from nucleic acid being sequenced. Of course, if required, more than one base may be removed, with the number of the bases at the end of the adaptor molecules being reduced by the number of additional bases (the number of additional predetermined bases) that it is required to remove. Thus, in the case of Bsa I a maximum of five bases can be removed. As will be seen below, later detection steps can, however, only analyze the bases in the overhanging strand and it is therefore appropriate not to leave less than one base beyond the recognition site. The number of new bases exposable for analysis in subsequent cycles is equal to the shortest distance between the recognition site and the cleavage site. In the case of Bsa1 this is one, but it is more that one in the cases of other enzymes, e.g. Fok1 where it is nine.

In FIG. 1, the nucleic acids to be sequenced in the population which is being examined (two for the purposes of illustration) have been independently immobilised to solid phase, exposing the non-immobilised ends to sequence analysis. The first stage in the overall process is that the thus-exposed ends are ligated to the adaptor molecules and residual adaptor molecules washed away. Bsa I is then added, and this effectively removes both the ligated adaptor and the preselected number of bases (as shown in the Figure, one base is removed). Enzyme and cleaved adaptor are then washed away.

In the next stage, a different population of adaptor molecules is employed. These adaptors are of the second of the two types mentioned above. These adaptor molecules have an extending strand in that portion of the molecule which is an oligonucleotide sequence, with the extending strand of each adaptor having a known and different base specificity. A population of adaptor molecules is employed that, in effect, is capable of reporting all possible combinations of permutations of predetermined base specificities. Moreover, each adaptor has both a detectable label which is specific for the particular base or bases which are predetermined in each adaptor and a nuclease recognition site as described above.

Preferably, the entire population of the second type of adaptors are then ligated to the cleavage product resulting from the previous stage of the process under conditions such that only adaptors where the extending strand exhibits actual complementarity for the extending overhang in the cleavage products will ligate. Such conditions, for example (but not essentially), could utilise 1 pmole of cleavage product, 200 pmoles of adaptors, and 0.25 units of T4 DNA ligase, at a temperature of 16° C. for 4 to 16 hours in a 50 ul reaction volume also containing 20 mM Tris-HC1 pH7.5 @ 24° C., 50 mM sodium chloride. 10 mM magnesium chloride, 1 mM adenosine triphosphate and 1 mM dithiothreitol. The conditions of time, temperature and ionic strength may be varied by one skilled in the art to achieve the required rates of ligation and specificity.

Of course, in the alternative each adaptor molecule at this stage could be ligated in turn with each nucleic acid sample being examined to determine whether it ligates or not. However, it is preferred that the population of adaptor molecules employed comprise molecules each having a different base specificity with a corresponding specific label. In this way, the adaptor molecules can be ligated simultaneously and, after washing away unused (unligated) adaptors, those adaptor molecules which have actually ligated can be determined and distinguished.

For the purposes of illustration in FIG. 1, the uppermost nucleic shown becomes green by ligating to the base C-specific adaptor molecule, while the lowermost nucleic acid shown (SEQ ID NOS: 36–37) becomes red by ligating to the base A-specific adaptor molecule.

Essentially, there are two ready options for analysis. In the first option, detection of the specific adaptor molecules which have successfully ligated with nucleic acid sequences can be performed whilst these molecules remain ligated. This is shown as Analysis Option 1 in FIG. 1. Such an option is preferred when many samples are being analyzed in the same reaction vessel, and the process can be both sensitive and inexpensive. Thus, nucleic acid samples could be immobilised each to separate one to five micron diameter beads which are generally commercially available. Over one million beads could then comfortably be analyzed using standard fluorescence microscopy coupled with image analysis. Reaction volumes would be very small, with consequent reduction in reagent costs. An alternative analysis option, Analysis Option 2 as shown in FIG. 1, exists once the products of ligation including the labelled adaptors are subjected to further action of the restriction enzyme, Bsa I. Because the adaptor molecules which are labelled also carry the recognition site for Bsa I, cleavage is again possible. As before, the recognition site is deliberately positioned in the oligonucleotide portion of such adaptor molecules such that one or more predetermined bases are removed from the end of each nucleic acid sequence being analyzed to leave an extending strand. In FIG. 1, Bsa I removes the adaptor molecules together with the end base from each nucleic acid. The number of bases removed at this stage of the process can obviously depend upon the positioning of the enzyme recognition sequence in much the same way as described above in relation to the first stages in the process.

In any event, as a result of the immobilisation of the original sequences to be determined, after the second Bsa I cleavage in the overall process a population of specific adaptors is released which can be analyzed for their particular labels in Analysis Option 2. Analysis of the labels produced by this process obviously gives base specific information derived from the nucleic acid sequences being analyzed.

In Analysis option 2, adaptor molecules may, if desired, be detected by the use of robotically controlled sampling and off-line detection. Robotic liquid handling is becoming commonplace in molecular biology applications (Uhlen, M., et al Trends in Biotech 10 p52–55 (1992)).

As can be seen from FIG. 1, the first cycle of ligation and analysis is now complete. Thus, after the first stage, each cycle of the process thus comprises ligation of labelled adaptors, followed by either: (a) detection of the particular label followed by removal of the adaptors plus a predetermined number of end bases from the nucleic acid sequence; or (b) removal of the adaptors plus one or more predetermined end bases from the nucleic acid followed by label detection.

To continue the process, a new cycle must be started. A new cycle of ligation of adaptor molecules is therefore performed as described before to determine which bases are now present at the degraded nucleic acid sequence ends. In FIG. 1, in the second cycle, the uppermost nucleic acid turns cyan through ligation of a base G-specific adaptor, and the lowermost nucleic acid turns blue through ligation of a base T-specific adaptor.

The process is repeated with cycles of ligation of labelled adaptors, washing and detection of labels and removal of adaptors to expose the next base or bases until the desired number of bases have been analyzed at the ends of the nucleic acids being examined or the entirety of the sequences have been determined.

At the very last stage, when the last base or bases is/are being determined it is, of course, optional and dependent upon other features of the process whether or not a final cleavage step is employed. Using Analysis Option 1, no final cleavage step is necessary.

It will be appreciated that the structure of the adaptor molecules which comprise oligonucleotide sequence is important to the sequencing process just described. In practice, the only limitation on the number of different adaptor molecules that can be employed is the number of distinguishably different labels that are available for determination of adaptor specificity at subsequent stages in the process. Availability of a large number of adaptor molecules which are individually specifically labelled has the advantage that more than one base at a time can be analyzed per cycle. Thus, by way of example, removing two bases at a time would require the use of 16 different adaptor molecules each having a different and distinguishable label. When 16 different labels are available, it is possible simultaneously to analyze all the possible products. In general terms, the number of adaptor molecules required is $4^n$, where n is the number of bases to be analyzed per nucleic acid per cycle.

It is also possible to analyze each base in the sequences more than once. This can be achieved by using more adaptor molecules than there are bases removed per cycle. For example, if during each cycle 16 different distinguishably labelled adaptors are used, each adaptor recognizing a unique combination of two different bases, then on the cycle that a given base is first exposed at the end of the nucleic acid being degraded and sequenced it is detected as a result of the specificity of the base at the extreme 5' end of the complementary bases in the labelled adaptor (see FIG. 1). However, one cycle later the same base will be detected by the penultimate base in the adaptor molecule.

The precise structure of the (second type—see above) adaptor molecules used in the above process is not critical, except that an oligonucleotide portion must obviously be included which has appropriate sequence to provide nuclease recognition site and one or more predetermined bases, and the adaptors must carry predetermined base-specific labels.

It is not essential that bases in adaptor molecules that are used to detect exposed bases in the nucleic acid sequence being degraded be at the extreme ends of the extending strands in the adaptors, merely that they are contained within the extending strand. The precise position of such base or bases merely determines when, in the overall process, they will be read.

Most preferably, adaptors in the invention are short double-stranded oligonucleotides which can be joined to the ends of cleavage products. They will have been chemically synthesised so that their sequence can be predetermined and so that large concentrations can be easily produced. They may also be chemically modified in a way which allows them to be easily purified during the process. Ideally their 5' ends will be unphosphorylated so that once joined to degraded nucleic acid fragments, the adaptored end of the latter will no longer be able to participate in further ligation reactions. The risk of inappropriate ligation involving adaptors is thus avoided.

Occasionally in the processes of the present invention which operate by sequential predetermined base removal, instances could arise where a new cleavage site for the restriction endonuclease(s) will be created by ligation of labelled adaptor to degraded nucleic acid sequence. This will be detected when more than one type of adaptor from the range of adaptors used will be able to ligate to the nucleic acid, unless the same bases are exposed by the respective cleavages which are occurring. In the latter case, this eventuality will be detected by the process during the cycle when the sequences diverge.

To eliminate the above mentioned possibility of new cleavage site formation, the use of enzyme recognition sites is avoided which can donate one or more bases in the direction of cleavage to one or more bases and create in the process an additional recognition site like the original but displaced (in the direction of cleavage) from the original. Furthermore, it is desirable to avoid placing, in the part of the adaptor which is between the recognition site and the cleavage site, one or more bases from the side of the recognition site which is away from the cleavage site in the order in which they occur in the recognition site, thus preventing the possibility of the nucleic acid being sequenced donating the necessary bases to create a new recognition site like the original recognition site but displaced from the original in the direction of cleavage. Other similar measures would be effective.

Figure 2B:
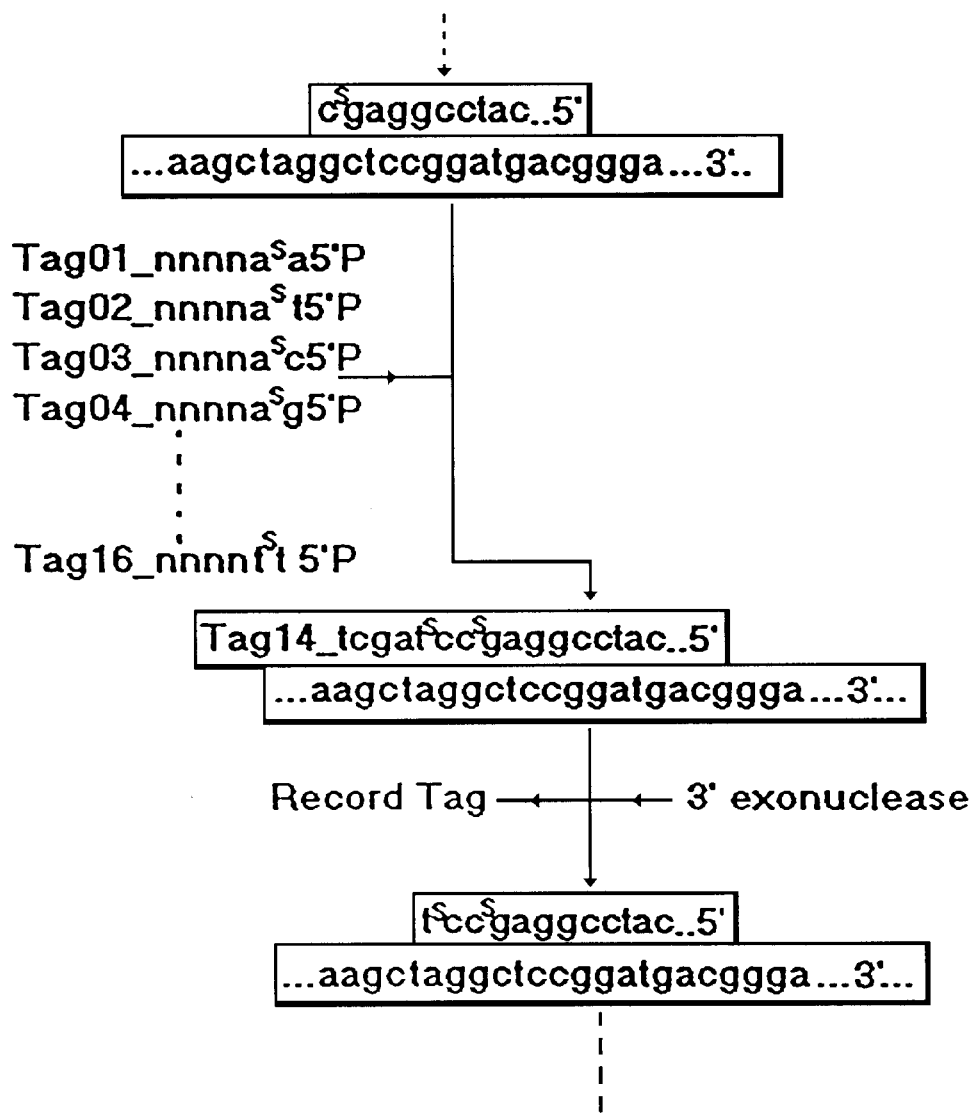

Moving on now to predetermined base addition processes of the invention, as has been indicated above the invention includes embodiments in which bases are added one or more at a time to an oligonucleotide primer which is annealed to a known sequence immediately adjacent to unknown nucleic acid sequence to be determined. This is generally illustrated in FIG. 2 (which shows sequencing of SEQ ID NO: 40), and is, of course, suited to single-stranded nucleic acids. After such annealing, the next stage in this particular set of embodiments is exposure of the duplex thus-created to ligation with a population of adaptors carrying one or more predetermined bases at the end of an oligonucleotide sequence. As with other embodiments of the invention, there is an interrelationship between the number of predetermined bases and the number of available labels used to detect the particular predetermined base or bases.

Apart from the oligonucleotide end of the adaptor molecules (which is critical to the extension process at the heart of such base addition embodiments for sequencing nucleic acids), the remainder of the structure of these particular adaptor molecules should ideally be non-specific to facilitate ligation, or need not even be nucleotide sequence provided that the actual nature of the molecule is such as not to interfere with the process of the invention.

As will be recalled, the next stage in the process is detection of the specific label or labels following adaptor ligation. This, of course, identifies the particular base or bases which have been added to the primer and, in turn, identifies the complementary bases in the nucleic acid strand which is being sequenced.

The final step in a cycle of this process is removal of all of the adaptor molecule except for the one or more predetermined bases which have extended the double stranded region of the primer/nucleic acid duplex. As will be appreciated, repeating cycles generates sequence information for the single stranded sequence being determined.

At the stage in each cycle when removal of the non-specific part of the adaptor molecules is effected, the means for doing this can be enzymatic or chemical with adaptor molecules designed accordingly. For example, positioning a phosphothionate linkage or linkages between the base(s) to be added to the duplex (the predetermined bases) and the non-specific part of the adaptors can be utilized (see Example 3) to permit an exonuclease to remove all but the predetermined bases.

The embodiments of the invention permit extremely high throughput, allowing hundreds of thousands of samples to be simultaneously processed. Applications therefore include, for example, analysis of highly complex nucleic acid samples up to whole genomes, or studying many different nucleic acids from many different individuals, for example when performing population or evolutionary studies or when studying complex linkage, especially of disease-associated traits, classifying microorganism types, or when determining total specific transcriptional activity of a cell or tissue. Diagnosis based on small percentages of base differences is also facilitated.

Preferably multiple nucleic acids to be sequenced are simultaneously and independently immobilised. A preferred way is to use adaptors which are oligonucleotides immobilised on beads or on a plate format, in particular glass beads or plates. Glass beads have the advantages that they are available in a wide range of mean diameters allowing optimum size to be selected, that conventional chemistries, especially oligonucleotide syntheses, can be used to attach labels, that once reacted they can be rendered inert, and that their shape can be highly irregular (allowing easy and repeated identification by image analysis). Plates have similar chemical advantages, and offer the advantage that a high density of samples can be arranged on a plate which is then a convenient format for reading in a scanning instrument.

It is generally impractical to subdivide large populations of nucleic acid fragments a sufficient number of times to allow individual fragments to be immobilised on a single type of bead. A mixed population of beads, synthesised such that each bead recognises only one type of fragment, therefore has to be prepared.

The presence of different oligonucleotides of sufficient length on each bead allows each bead to capture a different sequence by hybridisation. Methods well known in the art, if required, can be used to covalently link the captured sequences onto the oligonucleotides. Plates, or other materials in sheet format, can be derived/adapted to bind or covalently attach samples under investigation.

Ligations in the predetermined base addition overall process, as in other aspects of the invention, can be effected using DNA ligase.

In order to synthesise many different oligonucleotides simultaneously on glass beads so that only one type of oligonucleotide is found on a given bead a cyclical process is used. This is achieved by performing on beads a separate synthesis for each of the first bases required. The products of these syntheses are then mixed together and then divided into four separate synthesis reactions, one for each of the bases to be added. This cycle is repeated for as many positions as it is required to vary on the beads. A given bead can only have one combination of bases in its attached oligonucleotides because it is only ever exposed to one type of base addition per synthesis cycle. The actual order of bases is determined by the actual base additions to which a bead has been exposed. Cycles of this general type have been reported for simultaneously synthesising many different peptides on beads such that each bead has a single peptide (Lan, K., S., et al Nature 354 p82–84 (1991)).

To ensure that the oligonucleotide on each bead hybridises to only a single unique nucleic acid sequence, many more permutations of bases on the beads would be used than would be expected to occur in the set of fragments to be sequenced. Few beads would, therefore, detect a sequence in actuality. Thus, for practical purposes there would only be one type of fragment per occupied bead.

In relation to the kits of the invention, such kits can, of course, include other items as appropriate or desired, such as DNA ligase or such chemicals as may be required for effectively using oligonucleotide labels. The kits can, of course, also include written instructions.

The invention also includes any of the adaptor molecules described above in connection with the predetermined base addition process, and adaptors as described above for use in the predetermined base removal process of the invention.

The invention will now be further described by reference to specific exemplifying material.

EXAMPLES

All of the oligonucleotides used in these examples are synthesised, using the A.B.I. 380B, on a 1 $\mu$M scale or custom-synthesized commercially (Oswell Edinburgh). Synthesis is Trityl on unless modification by incorporation by biotin or an amino linker is performed. Biotin is incorporated where required, at the final (5') position of the oligonucleotide, during the synthesis, with a biotin phosphoramidite, (DMT- Biotin-C6-Phosphoramidite, Cambridge Research Biochemicals Incorporated), in which case oligonucleotides are made Trityl off. Fluorescent primers are made as required by incorporating amino linker at the appropriate position using Multi-Amino-C6-Phosphoramidite (Cambridge Research Biochemicals Incorporated) during synthesis. These are also made Trityl off. The actual dye is coupled later. Alternatively, the dye can be incorporated during synthesis by using the appropriate phosphormidate able to add a fluorescent label (A.B.I.). Other modifications as required include 5' end phosphorylation or the inclusion of a phosphorothioate linkage (Stec, W. J., Zon, G., Egan, W., and Stec, B. J. Amer. Chem. Soc. p6077–6079 (1984), Stec, W. J. and Zon, G., Tetrahedron Letters 25 p5275–5278 (1984), Stec, W. J. and Zon, G., J. Chromatography 326 p263–280 (1985)).

Phosphorylation is either chemical during synthesis, through the use of 5' Phosphate-ON (Cambridge Research Biochemicals Inc.) or enzymatic. Enzymatic phosphorylation is performed post synthesis and purification. Care is taken to ensure all traces of ammonia are removed otherwise enzymatic phosphorylation is inhibited. The additional use of a Biogel spin column below except with Tris HCl pH7.5 @24° C., 1 mM EDTA as running buffer is one means of ensuring ammonia removal. Enzymatic phosphorylation is performed for 30 minutes at 37° C. in a 25 ul reaction using 0.5 ug of oligonucleotide, 10 units of T4 polynucleotide kinase in 1 mM adenosine triphosphate, 10 mM magnesium chloride, 1 mM dithiothreitol, 10 mM Tris-HCl pH 7.5 @24° C. Purification is by extracting twice with an equal volume of phenol/chloroform 1:1 and passing through a Biogel P6 DSG resin spin column (see example 1) for which the buffer is TEA: 100 mM triethylamine acetate pH7 @25° C. Oligonucleotide in the eluate is dried in an aquavac for 2 hours at 50° C. and redissolved in water for use.

All oligonucleotides are deprotected at 55° C., in a water bath, for 8 to 16 hours. A few drops of 3M triethylamine acetate pH 7.0 @25° C. is first added to Trityl on oligonucleotides to protect the Trityl group. Oligonucleotides are then dried in a Rotary Evaporator at 50° C. or 35° C. for Trityl off or Trityl on, deprotected oligonucleotides, respectively. Oligonucleotides, except those with some form of modification, are redissolved in 0.5 ml HPLC grade water.

Each 60 ug of amino-linked oligonucleotide to be dye labelled is dissolved in 80 ul of 0.5M sodium bicarbonate buffer at pH 9.0. 6 ul of the appropriate dye esters (FAM-NHS ester, JOE-NHS ester, TAMRA-NHS ester or ROX-NHS ester, all A.B.I.), are added to the oligonucleotides on which they are required and incubation performed overnight at ambient in the dark. The dye coupled oligonucleotides are passed through a spin column (see example 1) and further purified by HPLC. The spin columns in this case use 100 mM TEA pH7.0 @25° C. as running buffer.

HPLC is conducted at a flow rate of 4.7 ml min$^{-1}$, using a Reverse Phase C18 Semi-prep column 5 u, 25 cm×1 cm (Beckman Ultrasphere), Buffer B (70% acetonitrile) and buffer A (100 mM triethylamine acetate pH 7.0). Oligonucleotide are filtered using a 0.22 uM filter, injected into the HPLC and purified according to the appropriate gradient in Table 1.

The largest peak (eluting between ca. 9 and 11 minutes) comprises the required oligonucleotide. The eluates are dried in the rotary evaporator at 500° C., and redissolved in 200 ul of HPLC grade water. Biotinylated oligonucleotides are now ready for use. Trityl on oligonucleotides are detritylated by adding glacial acetic acid to 80% and incubating for 20 minutes at ambient. An equal volume of absolute ethanol is added to the detritylated oligonucleotide which are then dried by rotary evaporation at 500° C. They are further purified by redissolving in 400 ul of HPLC grade water, and then precipitating for 30 minutes at room temperature by adding 40 ul of 3M sodium acetate pH 5.4 and 1000 ul of absolute ethanol. The pellet is collected in a microfuge at full speed for 20 minutes, dried at 37° C. and redissolved in 200 ul of water. It is then ready for use.

| Trityl on Oligonucleotides | | Biotinylated Oligonucleotides | | Dye Labelled Oligonucleotides | |
|---|---|---|---|---|---|
| % B | Duration (Minutes) | % B | Duration (Minutes) | % B | Duration (Minutes) |
| 15 | Initial | 10 | Initial | 15 | Initial |
| 15 | 3 | 10 | 2 | 15 | 2 |
| 15 to 40 | 5 | 10 to 20 | 5 | 15 to 20 | 2 |
| 40 | 8 | 20 to 21.2 | 7 | 20 to 28 | 12 |
| 40 to 95 | 2 | 21.2 to 90 | 2 | 28 to 95 | 2 |
| 95 | 2 | 90 | 1 | 95 | 1 |
| 95 to 15 | 1 | 90 to 10 | 3 | 95 to 15 | 3 |
| 15 | end | 10 | end | 15 | end |

EXAMPLE 1

Base Removal Sequence Analysis of the 1138 Base Pair NdeI to BsaI Restriction Fragment of pBR322, Using Solid Phase Capture.

There is a single site for the restriction endonuclease BsaI in the plasmid pBR322 at position 3429, Sutcliffe, J. G. Cold Spring Harbor Symp. Quant. Biol. (1978), p77–90. The recognition and cleavage by BsaI is

5' . . . GGTCTC(N)$_1$

3' . . . CCAGAG(N)$_5$

Its action on pBR322 therefore leaves a single-strand extension of 5' ACCG in the direction of the recognition site and 5' CGGT in the opposite direction.

This provides an opportunity to demonstrate the principles described in the sequencing process. NdeI also cleaves pBR322 once at position 2295. Of the two fragments produced from pBR322 by a BsaI/NdeI double digest, the BsaI created end of the fragment which lacks the BsaI recognition site can be immobilised to a solid phase and analysed by the sequencing process from the NdeI cut end.

Each lug of pBR322 used is digested to completion by 5 units of BsaI by incubation for 1 hour at 550° C. in a 25 ul reaction volume containing Restriction buffer: 50 mM potassium acetate, 20 mM Tris acetate, 10 mM magnesium acetate, 1 mM dithiothreitol pH 7.9 @24° C. The reaction is cooled to 37° C. and 10 units of NdeI are added to complete the double digestion by a further 1 hour incubation.

DNA is purified from the resultant mixture by extracting twice with an equal volume of phenol/chloroform 1:1, and then passing through a Biogel P6 DSG resin spin column, containing TE: Tris-HCl pH7.5, 1 mM EDTA. The unspun column has dimensions 1.5 cm high and radius 0.4 cm. Spinning is performed for 2.5 minutes at 2200 r.p.m in a Clinical Centifuge with a rotor radius of 145 mm.

The end to be joined to the solid phase is ligated to a biotinylated oligonucleotide adaptor which lacks a BsaI site:

5' Biotin GAACAGTCCACCTGTGT (SEQ ID NO: 1)

3' . . . CTTGTCAGGTGGACACAGCCA . . . Phosphate 5' (SEQ ID NO: 4)

This adaptors the BsaI produced end of the pBR322 fragment which lacks the BsaI recognition site. Simultaneously, the NdeI ends are ligated to a non biotinylated adaptor which contains a BsaI site in an appropriate configuration for being removed so as to leave ends which can be analysed by the reporter adaptors:

5' . . . TTGACAGGTGCACACGGACGGTCTCCCA (SEQ ID NO: 3)

3' . . . AACTGTCCACGTGTGCCTGCCAGAGGGT AT . . . Phosphate 5'.

This adaptor also inhibits the NdeI produced ends from religating back together.

The ligation reaction is performed using the fragments purified above in 50 ul of ligation buffer produced by adjusting the magnesium chloride to 10 mM, dithiothreitol to 1 mM, adenosine triphosphate to 1 mM, sodium chloride to 50 mM and Tris-HCl to 20 mM pH 7.5 @24° C. 2.5 units of T4 DNA Ligase and 200 pmoles of each of the adaptors are added and the reaction performed at 16° C. for 16 hours.

The ligated material is purified from the resultant mixture by extracting with an equal volume of phenol/chloroform 1:1, and then passing it according to the manufacturers instructions, through a Sephacryl S-400 Microspin column HR (Pharmacia), containing Restriction buffer less magnesium acetate. The unspun column has dimensions ca. 1.5 cm high and radius 0.4 cm. Spinning is performed for 2 minutes at 1850 r.p.m in a Clinical Centifuge with a rotor radius of 145 mm.

Magnesium acetate is added to 10 mM. 10 units of BsaI are added and incubation performed at 55° C. for 1 hour. This cleaves the adaptor with the BsaI site from the fragment to be analysed leaving the latter with 5' CATA single-strand extension.

The fragment to be analysed is next immobilised by binding to a streptavidin coated magnetic bead solid phase (Dynabeads M-280 Streptavidin, Dynal). The beads are gently resuspended and 20 ul of suspension removed to a 0.5 ml microfuge tube. Beads in the suspension are washed as follows. First they are sedimented by placing the tube in a Magnetic Particle Concentrator (MPC-E, Dynal) and the supernatant carefully removed. The tube is removed from the magnet and the beads gently resuspended in 40 ul of Binding/Washing buffer: 10 mM Tris-HCl pH 7.5 @25° C., 1 mM EDTA, 2 M sodium chloride. Washing is repeated twice more. 20 ul of Binding/Washing buffer is used to resuspend the beads after the final wash. These are then added to the restriction digestion above and the new suspension placed at 28° C. for 30 minutes with occasional gentle mixing to allow the biotin to bind to the beads.

The bead bound fragment is then washed 5 times as above except that the final resuspension is in 40 ul of ligation buffer (above). 200 pmoles of each of the reporter adaptors and 2.5 units of T4 DNA ligase are then added to allow those with specificity to the end of the immobilised fragment to ligate to the end of that fragment.

The four reporter adaptors are seperately synthesised and purified as described above, according to the format:

5' . . . Phosphate XN$_4$N$_4$GAGACCGAACAGTCCA CCTGTGTCACTG-Dye(n)-T (SEQ ID NOS: 5–8)

where X is one of the four bases A, C, G, or T with a different base in each case and Dye(n) is one of the dyes FAM, JOE, TAMRA or ROX with each dye corresponding to only one of the bases at position X. The A specific reporter adaptor is labelled with JOE whose fluorescence is detected through a filter with centre band of 560 nm, the C specific reporter is labelled with FAM whose fluorecence is detected through a filter with centre band of 531 nm, the G specific reporter is labelled with TAMRA whose fluorecence is detected through a filter with centre band of 580 nm, while the T specific reporter is labelled with ROX whose fluorecence is detected through a filter with centre band of 610 nm. The reporter adaptors are mixed in equal proportions and then equimolar amounts of the reporter adaptor mixture and the complementary oligonucleotide:

3' . . . CTCTGGCTTGTCAGGTGGACACAGTGAC (SEQ ID NO: 9)
are also mixed together.

Ligation is allowed to proceed for 6 hours at 16° C., and the unligated material removed by washing the beads 5 times using Washing/Binding buffer as described above except that the final resuspension is in 40 ul of Restriction buffer.

10 units of BsaI are added and incubation performed at 55° C. for 1 hour with occasional gentle mixing to remove the reporter adapter and one base from the immobilised fragment. The fragments on the beads are washed in readiness for another round of ligation to the reporter adaptor as described above, except that the reporter adaptor found in the first supernatant is purified.

Purification of the reporter adaptor is by extraction with an equal volume of phenol/chloroform and then passing through a Biogel spin column as described above except that the spin column buffer contains 100 mM triethylamine acetate pH7 @25° C. The eluate containing the released reporter is dried for 2 hours at 50° C. in an aquavac and the adaptor redissolved in 3.5 ul of 1:1 formamide/50 mM EDTA containing a visible amount of Dextran Blue and stored at 4° C. until analysed.

5 further cycles of ligation of the reporter adaptors, washing, cleavage by BsaI, washing and purification of the reporter adaptor removed into the supernatant by cleavage, all as described above, are performed.

Each of the reporter adaptor samples in formamide are analysed using an ABI model 373A DNA sequencing system. The samples are heated for 2 minutes at 90° C., placed on ice and then loaded onto a Base Sprinter gel, ran according to the manufacturers instructions. Concentration of pooled samples subject to the same treatment is performed or dilution is performed as required to gain the optimum signal strength using the DNA sequencing system. Samples are pooled by redissolving in the same aliquot of formamide/EDTA above while dilution, if necessary to obtain optimum signal strength, is also in the formamide. M13mp18 sequenced by the manufacturers dye primer chemistry according to the manufacturers instructions and the unused reporter adaptors are separately, simultaneously analysed as controls.

All of the reporter adaptors migrate at a rate equivalent to a 34 base sequence, allowing for the differences in mobilities imparted by the different dyes used. However, the wavelength at which they fluoresce is according to which reporter adaptor was able to ligate to the immobilised fragment during a given cycle. The first reporter removed by BsaI is detected through the 610 nm filter indicating that T on the reporter ligates opposite A on the immobilised fragment. The second reporter removed is detected through the 560 nm filter indicating that A on the reporter ligates opposite T on the immobilised fragment and that BsaI removes with the first reporter the A which is detected on the immobilised fragment by the previous reporter. The remaining reporters are detected through the 531, 580, 531 and 531 nm filters respectively in the order in which they are removed corresponding to C,G,C,C the remaining order of bases complementary to the bases removed at the end of the immobilised fragment sequenced. The full sequence at the end of the fragment is therefore 5' ATGCGG as predicted by Sutcliffe (ref. above), starting 3 bases from the 5' end which is the position of the first BsaI cleavage made possible by the original adaptor.

EXAMPLE 2

Base Removal Sequence Analysis of the 375 Base Pair EcoRI to BamHI Restriction Fragment of pBR322

As in example 1, advantage is taken of unique sites for restriction endonucleases in the plasmid pBR322, in this case for EcoRI and BamHI at position 4363/0 and 375 respectively, to demonstrate the principles described in the sequencing process, Sutcliffe, J. G. Cold Spring Harbor Symp. Quant. Biol. (1978), p77–90.

Each lug of pBR322 used is digested to completion by 5 units each of EcoRI and BamHI by incubation for 2 hours at 37° C. in a 25 ul reaction volume containing Restriction buffer: 50 mM potassium acetate, 20 mM Tris acetate, 10 mM magnesium acetate, 1 mM dithiothreitol pH 7.9 @24° C.

The 375 base pair fragment is purified from the resultant mixture by extracting with an equal volume of phenol/chloroform 1:1, and then passing it through a Sephacryl S-1000 column (Pharmacia) run according to gel filtration conditions. The column dimensions are radius 0.4 cm and height 5 cm. The running buffer is TE: Tris-HCl pH 7.5 @24° C., 1 mM EDTA plus the addition of sodium chloride to 50 mM and the capacity is >5 ug. 100 ul fractions are collected and 5 ul samples from each fraction analysed by agarose gel electrophoresis (Sambrook, J., Fritsch, E. F. and Maniatis, T. ed (1989). "Molecular Cloning". Cold Spring Harbor Laboratory Press, New York) for the presence of the required fragment. Peak containing fractions are pooled, avoiding the larger fragment present and the DNA precipitated for 30 minutes at room temperature by adding $\frac{1}{10}$th volume of 3M sodium acetate pH 5.4 and 2.5 volumes of absolute ethanol. The pellet is collected in a microfuge at full speed for 20 minutes, washed once with 70% ethanol and dried at 37° C. The pellet is then redissolved for use at 0.5 ug $ul^{-1}$ in TE.

The EcoRI end to be sequenced is ligated to an adaptor which contains a BsaI site in an appropriate configuration for being removed so as to leave ends which can be analysed by the reporter adaptors:

5' . . . TTGACAGGTGCACACGGACGGTCTCCCA (SEQ ID NO: 10)

3' . . . AACTGTCCACGTGTGCCTGCCA-GAGGGTTTAA . . . Phosphate (SEQ ID NO: 11)

Simultaneously, the BamHI end is ligated to an adaptor which lacks a BsaI site:

5' . . . GAACAGTCCACCTGTGT (SEQ ID NO: 12)

3' . . . CTTGTCAGGTGGACACACTAG . . . Phosphate 5' (SEQ ID NO: 13)

The adaptors also inhibit the BamHI and EcoRI produced ends from religating back together.

The ligation reaction is performed using the fragment purified above in a 50 ul reaction volume containing 2 ug of fragment with the addition of magnesium chloride to 10 mM, dithiothreitol to 1 mM, adenosine triphosphate to 1 mM, sodium chloride to 50 mM and Tris-HCl to 20 mM pH 7.5 @24° C., producing ligation buffer. 0.25 units of T4 DNA Ligase and 2 pmoles of each of the adaptors are added and the reaction performed at 16° C. for 16 hours.

The ligated fragment is purified from the resultant mixture by extracting with an equal volume of phenol/chloroform 1:1, and then passing it according to the manufacturers instructions, through a Sephacryl S-400 Microspin column HR (Pharmacia), containing Restriction buffer above but lacking magnesium. The unspun column has dimensions ca. 1.5 cm high and radius 0.4 cm. Spinning is performed for 2 minutes at 1850 r.p.m in a Clinical Centifuge with a rotor radius of 145 mm.

Magnesium acetate is added to 10 mM to the eluate. 10 units of BsaI are added and incubation performed at 55° C. for 1 hour. This cleaves the adaptor from the fragment to be immobilised leaving the fragment with a 5' CAAA single-stranded extension.

The newly digested material is purified by extracting with an equal volume of phenol/chloroform 1:1, and then passing it according to the manufacturers instructions, through a Sephacryl S-400 Microspin column HR (Pharmacia) as described above but containing ligation buffer.

200 pmoles of each of the reporter adaptors and 0.25 units of T4 DNA ligase are then added to allow those with specificity to the BsaI cut end of the purified fragment to ligate to the end of that fragment.

The four reporter adaptors are seperately synthesised and purified as described above, according to the format:

5'... Phosphate $XN_4N_4N_4$GAGACCGAACAGTCCACC TGTGTCACTG-Dye(n)-T (SEQ ID NO: 5–8)

where X is one of the four bases A, C, G or T with a different base in each case and Dye(n) is one of the dyes FAM, JOE, TAMRA or ROX with each dye corresponding to only one of the bases at position X. The A specific reporter adaptor is labelled with JOE whose fluorecence is detected through a filter with centre band of 560 nm, the C specific reporter is labelled with FAM whose fluorecence is detected through a filter with centre band of 531 nm, the G specific reporter is labelled with TAMRA whose fluorecence is detected through a filter with centre band of 580 nm, while the T specific reporter is labelled with ROX whose fluorecence is detected through a filter with centre band of 610 nm. The reporter adaptors are mixed in equal proportions and then equimolar amounts of the reporter adaptor mixture and the complementary oligonucleotide:

3' ... CTCTGGCTTGTCAGGTGGACACAGTGAC are also mixed together.

Ligation is allowed to proceed for 6 hours at 16° C., and the unligated material removed by extracting with an equal volume of phenol/chloroform 1:1, and then passing it according to the manufacturers instructions, through a Sephacryl S-400 Microspin column HR (Pharmacia) as described above but containing Restriction buffer.

10 units of BsaI are added and incubation performed at 55° C. for 1 hour to remove the reporter adapter and one base from the immobilised fragment. The digested fragment is purified in readiness for another round of ligation to the reporter adaptor by extracting with an equal volume of phenol/chloroform 1:1, and then passing it according to the manufacturers instructions, through a Sephacryl S-400 Microspin column HR (Pharmacia) as described above but containing 100 mM triethylamine acetate pH7.0 @24° C. (TEA). Addition of fresh 50 ul aliquots of TEA to the microspin column and centifuging between each addition as above is continued (1 to 4 more times) to elute the reporter cleaved from the fragment. The reporter and the fragment are separately dried in an aquavac at 500° C. for 2 hours. The reporter is redissolved in 3.5 ul of 1:1 formamide/50 mM EDTA containing a visible amount of Dextran Blue and stored at 4° C. until analysed.

The fragment is dissolved in 50 ul of ligation buffer and subjected to 5 further cycles of ligation of the reporter adaptors, purification, cleavage by BsaI, purification of the fragment and purification of the reporter adaptor removed by cleavage, all as described above.

Each of the reporter adaptor samples in formamide are analysed using an ABI model 373A DNA sequencing system. The samples are heated for 2 minutes at 90° C., placed on ice and then loaded onto a Base Sprinter gel, ran according to the manufacturers instructions. Concentration of pooled samples subject to the same treatment is performed or dilution is performed as required to gain the optimum signal strength using the DNA sequencing system. Samples are pooled by redissolving in the same aliquot of formamide/EDTA above while dilution is also in the formamide. M13mp18 sequenced by the manufacturers dye primer chemistry according to the manufacturers instructions and the unused reporter adaptors are separately, simultaneously analysed as controls.

All of the reporter adaptors migrate at a rate equivalent to a 34 base sequence, allowing for the differences in mobilities imparted by the different dyes used. However, the wavelength at which they fluoresce is according to which reporter adaptor was able to ligate to the immobilised fragment during a given cycle. The first reporter removed by BsaI is detected through the 610 nm filter indicating that T on the reporter ligates opposite A on the immobilised fragment. The second reporter removed is detected through the 560 nm filter indicating that A on the reporter ligates opposite T on the immobilised fragment and that BsaI removes with the first reporter the A which is detected on the immobilised fragment by the previous reporter. The remaining reporters are detected through the 560, 580, 560 and 580 nm filters respectively in the order in which they are removed corresponding to A,G,A,G the remaining order of bases complementary to the bases removed at the end of the immobilised fragment sequenced. The full sequence at the end of the fragment is therefore 5' ATTCTC as predicted by Sutcliffe (ref. above), starting 2 bases from the 5' end which is the position of the first BsaI cleavage made possible by the original adaptor.

EXAMPLE 3

5' to 3' Sequence Analysis of M13mp18

M13mp18 is a single-stranded DNA of known sequence (Messing, J., Methods in Enzymology 101 (Part C) Recombinant DNA p20–78 (1983) Wu, R., and Moldave, K. (eds). Academic Press, New York). It is therefore a suitable substrate for demonstrating the process of sequencing using reporter adaptors which add bases during each sequencing cycle.

M13mp18 single-stranded DNA is annealed to the forward sequencing primer:

3' TGACCGGCAGCAAAATG (SEQ ID NO: 14).

Each ug of M13 DNA is added to 2 pmoles of primer in 20 ul of Annealing buffer: 10 mM Tris-HCl pH7.5 @24° C., 50 mM sodium chloride. The reaction is heated to 95° C. for 2 minutes and then cooled to 55° C. for 30 minutes.

The annealed template/primer is ligated to the reporter adaptors. Each reporter adaptor is separateley synthesised and purified. The first 15 of the oligonucleotides are tagged according to the Plex Tags (Millipore):

Tag_01 ATATATATCCCATAATCCACnnnnAsA 5' phosphate (SEQ ID NO: 15)

Tag_02 CATTCTATTCTAAATCACTCnnnnAsC 5' phosphate (SEQ ID NO: 16)

Tag_03 TCTTCAATTACATCCCAACCnnnnAsG 5' phosphate (SEQ ID NO: 17)

Tag_04 TCAAATCACCTACCCACAACnnnnAsT 5' phosphate (SEQ ID NO: 18)

Tag_05 AAACACTAAACTCAATACACnnnnCsA 5' phosphate (SEQ ID NO: 19)

Tag_06 CATCATTCCAAACAACAATCnnnnCsC 5' phosphate (SEQ ID NO: 20)

Tag_07 CTATATCCAACCATCTTCCCnnnnCsG 5' phosphate (SEQ ID NO: 21)

Tag_08 CCCACACTATTTCACATTCCnnnnCsT 5' phosphate (SEQ ID NO: 22)

Tag_09 AAAAACCCTTAATCAAAAACnnnnGsA 5' phosphate (SEQ ID NO: 23)

Tag_10 TCATCCCAACCAACACCAACnnnnGsC 5' phosphate (SEQ ID NO: 24)

Tag_11 ACTCATATAACTACTAATCCnnnnGsG 5' phosphate (SEQ ID NO: 25)

Tag_12 AACACAATTTACAACCAAACnnnnGsT 5' phosphate (SEQ ID NO: 26)

Tag_13 CACTATTCATCTCAACCAACnnnnTsA 5' phosphate (SEQ ID NO: 27)

Tag_14 TCACACTCCAAATTTATAACnnnnTsC 5' phosphate (SEQ ID NO: 28)

Tag_15 TCCCAAATCCAATATAATACnnnnTsG 5' phosphate (SEQ ID NO: 29)

Tag_16 AAGGAAAATGTGGTGGAATGnnnnTsT 5' phosphate (SEQ ID NO: 30)

n corresponds to all four bases at a given position and s corresponds to a phophorothioate linkage.

The annealing reaction is adjusted to Ligation buffer by adding Tris-HCl pH7.5 @24° C. to 20 mM, sodium chloride to 50 mM, dithiothreitol to 1 mM, magnesium chloride to 10 mM and adenosine triphosphate to 1 mM.

The reporter adaptors are mixed in equimolar proportions and then the mixture added to the ligation reaction. The reporter adaptor mixture is added in a molar ratio of 100:1 of M13mp18 DNA.

0.25 units of T4 DNA ligase is added and incubation performed for 6 to 16 hours at 16° C.

M13 plus ligated reporter adaptor are purified from the ligation mixture using the LacZ Vector Purification Kit (Dynal) according to the manufacturers instructions except that the ligation reaction is the starting point rather than a phage supernatant, 100 ul of beads suspension (Dynabeads M-280 Streptavidin, Dynal) are used with 25 pmoles of custom prepared oligonucleotide which is identical to the oligonucleotide on the supplied beads except that the three 3' most nucleotides are joined by phosphorothioate linkages so that they are exonuclease resistant, four washes are performed and 20 ul of elution buffer are used. Eluate equivalent to 100 ng of M13mp18 DNA is removed as a sample to determine which reporter adaptor ligated.

The remainder of the eluate is prepared for further rounds of reporter addition. T4 DNA polymerase is used to remove the TAG, so that the remainder of the reporter can be subject to the action of Exonuclease III. The eluate is adjusted to Pol/Exo buffer by the addition of Tris-HCl pH7.5 @24° C. to 20 mM, magnesium chloride to 10 mM, dithiothreitol to 1 mM and sodium chloride to 50 mM. The new mixture is divided into four equal aliquots. To each is added three different deoxyribonucletides to 0.1 mM each. The deoxyribonucleotides are added such that each reaction misses a different base. This prevents extensive polymerisation from occuring once the TAG has been removed and also covers the possibility that entirely one type of base could be found in the double-stranded region between the TAG and the specific bases. By dividing the reaction into four different types, when the aforementioned situation does arise, loss of the double stranded region will only occur for 25% of the remaining eluate. 1 unit of T4 DNA polymerase is added and incubation performed at 37° C. for 30 minutes. DNA is purified from the reaction using the LacZ Vector Purification Kit as described above, except that no sample is removed.

Exonuclease III is used to remove from the remainder of the M13 DNA, the remainder of the reporter adaptor up to the phosphorothioate linkage. Two additional bases are therefore left on the primer. The eluate is adjusted to Exonuclease III buffer by the addition of Tris-HCl pH8.0 @24° C. to 50 mM, magnesium chloride to 5 mM and 2-mercaptoethanol to 10 mM. 0.1 unit of exonuclease III is added and incubation is performed at 37° C. for 10 minutes. DNA is purified from the reaction mixture using the LacZ Vector Purification Kit as described above, except that no sample is removed.

5 further rounds of ligation to the reporters, purification, removal of sample for analysis of the TAG present, treatment with T4 DNA polymerase, purification, treatment with exonuclease III and purification are performed, ending with sampling during the final cycle.

To examine the reporters present at each cycle they are divided into 8 equal proportions, spotted individually onto 8 Nylon membranes with one of each sample per membrane. 5 ng of each of the original reporter adaptors are also spotted separately onto each membrane as a control. The membranes are probed by hybridisation, washed and finally detected by autoradiography, all methods including spotting are according to standard procedures (Sambrook, J., Fritsch, E. F. and Maniatis, T. ed (1989). "Molecular Cloning". Cold Spring Harbor Laboratory Press, New York).

Oligonucleotides complementary to the last 3' most sequences (Plex Tags) of the reporter adaptors are used as probes. Each oligonucleotide is synthesised separately and labelled by T4 polynucleotide kinase with gamma $^{32}$P adenosine triphosphate.

The membranes are probed as follows:

First membrane with the oligonucleotide complementary to Tag_07

Second membrane with the oligonucleotide complementary to Tag_02

Third membrane with the oligonucleotide complementary to Tag_09

Fourth membrane with the oligonucleotide complementary to Tag_14

Fifth membrane with the oligonucleotide complementary to Tag_12

Sixth membrane with the oligonucleotide complementary to Tag_02

Seventh membrane with the oligonucleotides complementary to Tags that have not already been used. The specific activity of each oligonucleotide is maintained the same as in the previous probings so that in this case, eleven times more probe is used overall.

Eighth membrane with the oligonucleotides complementary to Tag_02, Tag_07, Tag_09, Tag_12, and Tag_14. Again, the specific activity of the individual probes are maintained so that overall five times more probe is used.

The positions of Tag_07 and the first sample are primarily labelled on the first membrane indicating that the reporter adaptor corresponding to CG was incorporated during the first ligation. The positions of Tag_02 and the second and sixth samples are primarily labelled on the second membrane indicating that the reporter adaptor corresponding to AC was incorporated during the second and sixth ligations. Furthermore, the 3' end of the primer was no longer the same after the first exonuclease treatment. Similarly, the positions of Tag_09 and the third sample, Tag_14 and the fourth sample, Tag_12 and the fifth sample and Tag_02 and the second and sixth samples are labelled on the third, fourth, fifth and sixth membranes, respectively. This indicates that the reporter adaptors corresponding to GA, TC, GT, and AC were incorporated respectively, one per each cycle from the third cycle. It also suggests that the sequence is 5' GCCAAGCTTGCA from the 3' end of the primer and that the two bases at the 5' end of each Tag were left behind following the exonuclease treatment during the cycle that the TAG was incorporated.

The final two membranes serve as a control to demonstrate that the only oligonucleotides which will detect the samples and the TAGs are those which are expected to be complementary to them.

As will be appreciated from the above, included in the present inventive concept is the idea that beads, which may be randomly chosen, each with their own unique oligonucleotide attached can be used for ordering nucleic acids for sequencing purposes. The use of irregular beads enables benefit to be taken from the individual optical signature which each such bead possesses. The ability to correlate between nucleic acids and particular unique beads obviates the need for more formal arrays of nucleic acids. The invention includes this concept and uses thereof.

Of course, the beads are readily available and standard chemical techniques known to those in the art can be used for linking with oligonucleotides.

EXAMPLE 4

Figure 3A:
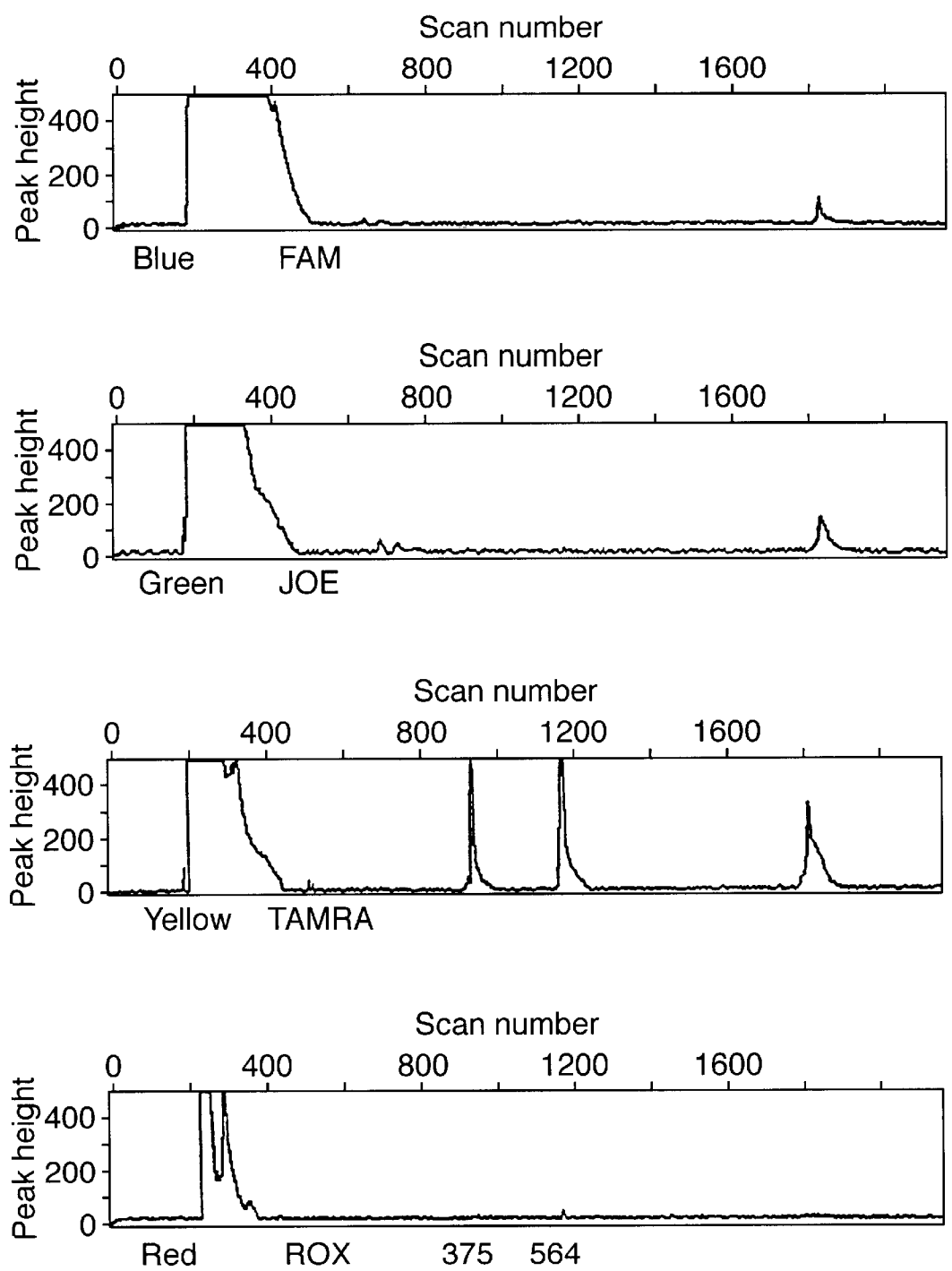
Figure 3B:
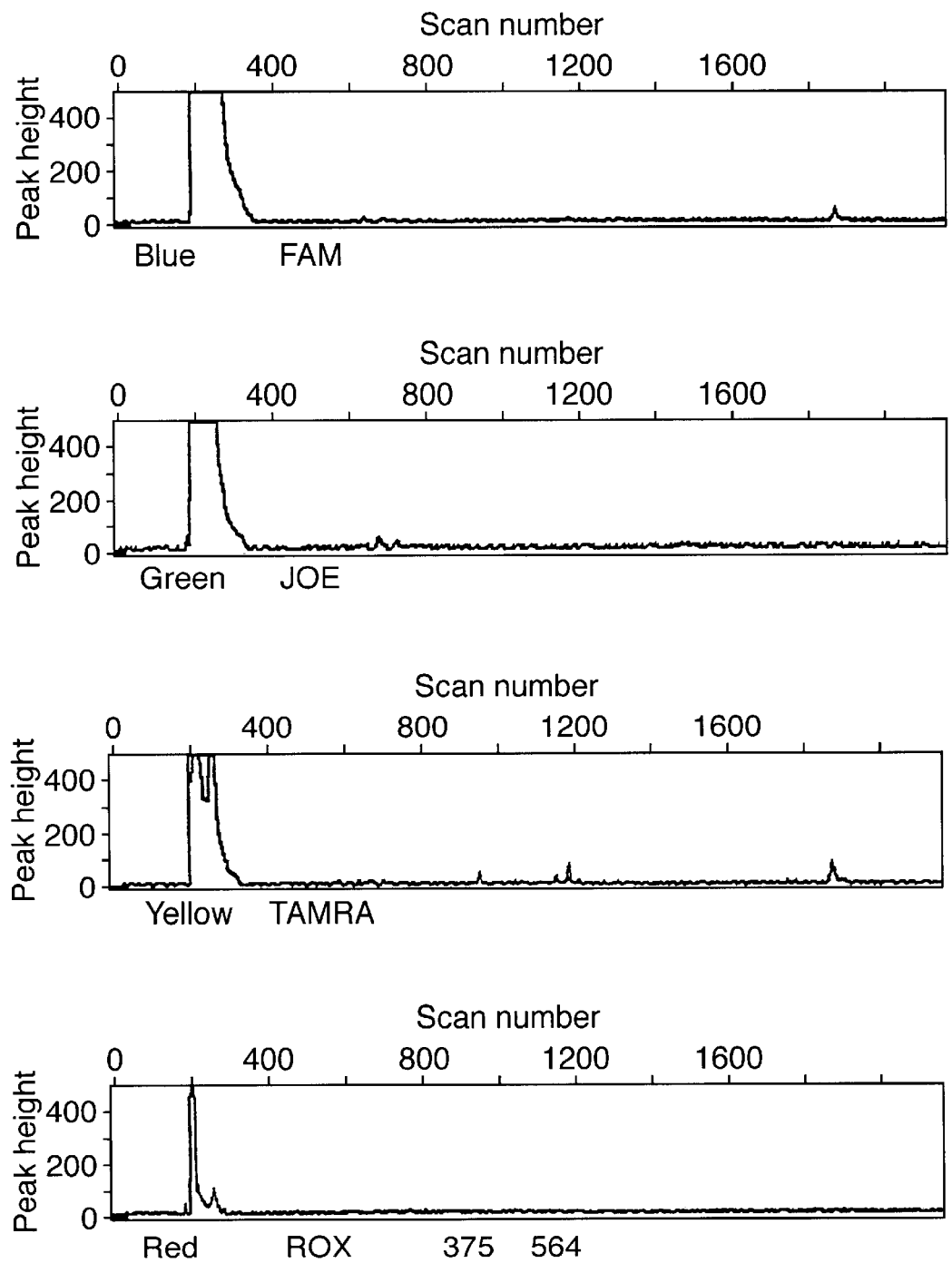

In relation to this Example, the accompanying FIG. 3(a) is an electropherogram of BamH1 to EcoR1 and BamHI to Eag1 fragments of pBR322, previously labelled during a first cycle of ligation to reporter adaptors, and showing expected specific labelling by the TAMRA reporter. FIG. 3(b) is an electropherogram of BamH1 to EcoR1 and BamH1 to Eag1 fragments of pBR322, previously labelled during a first cycle of ligation to reporter adaptors, and then cut by Bsa1, showing expected removal by the endonuclease of the specific labelling by the TAMRA reporter.

45 $\mu$g of pBR332 per digest were cut to completion by 450 units each of EcoR1 and Eag1 for 2 hrs at 37° C. in 450 $\mu$l of 100 mM NaCl, 50 mM Tris-HCI, 10 mM MgCl$_2$ 1 mM DTT pH7.9 at 25° C. 2 $\mu$l of the digest were examined by agarose gel electrophoresis to confirm digestion. The fragments produced were purified by extracting with an equal volume of 1:1 phenol/chloroform twice followed by an equal volume of chloroform, the aqueous phase being retained in each case. Two minutes microcentrifugation were used to separate the phases which were mixed initially by vortexing for 30 seconds.

The DNA was precipitated by adding 1/10 volume of 3M Na acetate pH 5.3 and 2.5 volumes of the new volume of 100% ethanol. After about 30 minutes at −20° C. the precipitate was collected by microcentrifugation at 15000×g for 15 minutes. The supernatant was discarded and the pellet washed with 1 ml of 70% ethanol. Centrifugation was repeated for 5 minutes and the supernatant again discarded. Residual liquid was removed using a Gilson tip after a brief microcentrifugation to collect it at the bottom of the tube. Care was taken to avoid removing the pellet at any stage. The pellet was dried at 37° C. for 10 minutes and then re-dissolved in 92 $\mu$l of TE: Tris-HC1 10 mM pH 7.5 at 20° C. and 1 mM EDTA.2 $\mu$l were examined by agarose gel electrophoresis to check recovery. It was necessary to vortex the TE throughout the tube which contained the pellet to ensure that all traces became dissolved.

Two oligonucleotide pairs were prepared as described previously for the purpose of blocking the majority of the EcoR1 and Eag1 cohesive ends:

5' AATTCGGAGTGAAAGCG 3' (SEQ ID NO: 31)

5' GCCTCACTTTCG 5' (SEQ ID NO: 32)

and

5' GGCCGGCCTGACTCT 3' (SEQ ID NO: 33)
CCGGACTGAGAG 5'(SEQ ID NO: 34)

respectively.

15 pmoles of each of the blocking oligonucleotides were ligated to the cut and purified pBR322 in a 360 $\mu$l reaction at 22° C. for 1.5 hours containing 3.6 units of T4 DNA ligase, 10 mM Tris-HCI pH7.5 @22° C., 50 mM BaCl, 10 mM MgCl$_2$, 1 mM DTT, 1 mM ATP. The ligase was added last and the reaction heated to 65° C. and then cooled to ambient to aneal the oligonucleotides prior to its addition. 1/60 of the reaction was prepared as a control without the oligonucleotides and analysed by agarose gel electrophoresis alongside 1/60 of the main reaction to confirm that concatamerisation could occur in the absence of the blocking oligonucleotides. After ligation, DNA was purified from the main reaction by extracting twice with phenol/chloroform as described above and then divided equally between 4 S-400 MicroSpin columns (Pharmacia), run according to the manufacturers instructions at 1850 cpm for 2 minutes in a clinical centrifuge with a rotor radius of 145 mm. The resultant eluates were pooled and the 939 base pair EcoR1 to Eag1 fragment cut by 240 units BamH1 at 37° C. for 1 hour, in a 600 $\mu$l reaction containing NaCl and MgCl$_2$ added to 50 mM and 10 mM respectively. This had the effect of creating two BamH1 cohesive ends on different fragments whose opposite ends could no longer participate in ligation.

1/30 of the reaction was set up without BamH1 as an uncut control and compared to 1/30 of the digest by agarose gel electrophoresis to confirm that bands of 375 and 564 base pairs were produced from the original 939 base pair fragment. The main reaction was purified by phenol extraction and ethanol precipitation and re-dissolved in 90 $\mu$l TE as described above, except that the 70% ethanol wash was omitted. Low molecular weight material, especially oligonucleotides were further removed by passing the new solution through a sephacryl S-1000 (Pharmacia) column run at 15–20 cm of water pressure. The column had dimensions 5 cm high and 1 cm diameter. Peak fractions were determined by agarose gel electrophoresis, pooled and ligated overnight to the labelled reporter adaptors, to commence a first cycle of ligation of reporters to be followed by cutting. Had the oligonucleotides not been removed, they would have competed for ligation to the labelled reporter adaptors. The reporter adaptors were as described in Examples 1 and 2. It had been empirically determined that a ratio of between 0.3 to 1 pmole of digested pBR322 to between 64 to 320 pmoles of each of the reporter adaptors, in a 100 $\mu$l ligation gave specific labelling of the pBR322 fragments as determined by a fluorescence gel reader. This probably reflected the fact that too low a concentration of adaptors failed to block concatamerisation of the pBR322, while too high a concentration of adaptors reduced the yield of labelled product, probably because the adaptors have a 5' phosphate and are therefore able to ligate to each other thus lowering their effective concentration. Alternative strategies would utilise unphosphyrylated adaptors to eliminate the latter effect. Should the nicked DNA which resulted between ligation of such adaptors and the fragment of interest not be tolerated for some reason by the process, a kinase plus ligation step could be used to repair the nick after removal of the reporter adaptors.

Ligation was conducted in a 2400 $\mu$l volume containing 1875 pmoles of each reporter adaptor, 10 mM Tris-HC1 pH 7.5 at 22° C., 10 mM MgCl$_2$, 50 mM NaCl, 1 mM DTT, 1 mM ATP and 24 units of T4 DNA ligase for 16 hours at 16°

C. The ligase was added last and prior to its addition the reaction was heated to 65° C. for 5 minutes then cooled to ambient to aneal the oligonucleotides. A control was set up from other equivalent reactions containing amounts corresponding to $\frac{1}{10}$ of the S-1000 eluate (ligase control). Controls from other equivalent reactions were also set up containing amounts corresponding to $\frac{1}{10}$ of the S-1000 eluate. In these, the same final concentrations of reporter oligonucleotide were used but were made but were made up entirely of only one of the reporters i.e. 4× the original concentration of a given reporter was used and none of the other reporters.

After ligation, fragments in each reaction were purified by extraction twice with phenol/chloroform and ethanol precipitation as described above except that the 70% ethanol wash was omitted. The control reactions were re-dissolved in 100 $\mu$l of TE each and the main reaction in 205 $\mu$l of TE. 5 $\mu$l of the 205 $\mu$l were examined on an agarose gel to check recovery. The bulk of the reporter adaptors were removed by passing through a SizeSep 400 Spin Column (Pharmacia) run according to the manufacturers instructions at 1550 rpm for 2 mins in a 145 mm radius rotor. 100 $\mu$l were loaded on each column so that two columns were required for the main reaction. The column dimensions were approximately 0.8 cm diameter and 3 cm high. Columns was equilibrated before use with 8 mls of TE+50 mm NaCl, flowing under gravity.

Half of the eluate from the control reactions and all but $\frac{1}{12}$ of the total pooled eluate from the main reaction were digested by Bsa1 to remove the reporter adaptors, and the end base of the fragment ligated to the reporters. Digests were performed in Bsa1 buffer (NEB) at 55° C. for 1.5 hrs containing 20 units per 100 $\mu$l of Bsa1 . Digests were performed in approximately twice the volume originally added to the columns. Bsa1 was added last and $\frac{1}{40}$ of the reaction was sampled prior to adding the enzyme to examine on an agarose gel as an uncut control. Similarly $\frac{1}{40}$ of the reaction was also examined after the reaction to confirm that digestion had occurred. Bsa1 cuts the 3323 Eag1 to EcoR1 fragment of pBR322 to give a 929 base fragment and a 2494 base fragment. These fragments appear to be slightly larger because of the adaptors added to the EcoR1 and Eag1 ends.

The digest from the control reactions and $\frac{1}{12}$ of the digest from the main reaction were purified by extraction twice with phenol/chloroform and ethanol precipitation as described above, except that the 70% ethanol wash was omitted. The undigested samples from the control reaction and the sample corresponding to $\frac{1}{12}$ of the undigested main reaction were similarly purified, except that the phenol/chloroform extractions were also omitted. The precipitated samples were retained for analysis by a fluorescent gel reader, see below.

The main reaction was extracted twice by phenol/chloroform as described above and further purified by passing through S-400 MicroSpin columns as described above. The remaining reaction totalled approximately 400 $\mu$l and 100 $\mu$l was used for each of four columns. This completed the first cycle of ligation of reporters followed by cutting to expose the next base for analysis. A second cycle of ligation of adaptors then cutting was commenced. New reporters were ligated to the newly generated cohesive ends in the purified main reaction. The total eluate equalled 480 $\mu$l. Ligation was performed as for the first main reporter ligation, with the same proportions of reactants but scaled accordingly for a final reaction volume of 600 $\mu$l.

This ligation was purified, ethanol precipitated and the oligonucleotides removed by SizeSep 400 Spincolumns as described for the first main reporter ligation. Bsa1 digestion was performed as previously described except that $\frac{1}{6}$ of the reaction was sampled as an uncut control and post digestion $\frac{1}{6}$ of the reaction were sampled as a cut control. The two samples were purified and stored as ethanol precipitates as described for the samples after the first reporter ligation.

The remaining Bsa1 cut material was also purified and ligated to new reporter adaptors as previously described to commence a third cycle of ligation then cutting. Purification and Bsa1 digestion was performed as previously described except that half the first eluate was retained as an uncut control, and the remainder was digested by Bsa1 . The cut sample was purified by phenol/chloroform extraction as described and then both samples were recovered by ethanol precipitation as described above. This completed the third cycle of ligation and cutting.

It proved appropriate to take as samples increasing proportions of the main reaction during each successive cycle to allow for the losses which occurred during each cycle, particularly through the columns. Losses were most pronounced for the smaller fragments, presumable reflecting the size-separating properties of the columns used. It would therefore be preferred in such embodiments to use larger fragments for analysis. A Bsa1 and Eag1 cut fragment of pBR322 that had their ends blocked before cutting with EcoR1 would be one instance of how this could be achieved. The fragments need to be large enough to be retained during the purification but not so large that they cannot be resolved in the analysis which follows. 900 to 1800 base pairs is a suitable range. An alternative strategy was also adopted in very similar experiments. In this case large fragments were processed, and then samples were cut with a restriction endonuclease which produced smaller fragments suitable for analysis and on which the ends of interest could be found. For example, the Nde1 to Bsa1 fragment of pBR322 was used. In this case, the Bsa1 produced end nearest the Nde1 site was blocked prior to use of the reporter adaptors. Taq1 was then used to produce fragments which were suitable for analysis from samples which had been taken during the cycling process.

The ethanol precipitates corresponding to each sample were re-dissolved in 3 $\mu$l of TE and the 3 $\mu$l of gel loading buffer: formamide, 50 mm EDTA plus visible amount of Dextran Blue. Each sample was analysed by electrophoresis using the A.B.I. 373A according to the manufacturers instructions. Short plates (6 cm well to read) were used. Electrophoresis was at 30 watts for 3.5 hours using a 6% polyacrylamide gel polymerised with 0.5% ammonium persulphate and 0.05% TEMED. The unpolymerised gel solution was prepared using 80 g urea, 24 ml 40% 29:1 Acrylamide:Bisacylamide, 60 mls Milli Q grade water (Millipore) and 2 g mixed bed ion exchange resin. Stirring was performed for 30 minutes and then solid material removed by filtration through a 0.2 $\mu$m Nalgene filter. 16 ml TBE (108 g Tris base, 55 g Boric acid and 8.3 g $Na_2$EDTA per liter) and water were added to 160 ml and degassing performed.

24 cm well to read (large plates) were used when greater resolution was required. Samples were diluted in gel loading buffer if signal intensities were too great. Electropherograms were scaled according to the largest peak which was usually unincorpated reporters. Dye scales were therefore reduced in height to enhance small peaks, where necessary.

Filter set A was used and Rox 350, Rox 500, Rox 1000, Rox 2500 were also ran as size markers. Genescan 672 collection was run during electrophoresis and Genescan 672 analysis was used for analysis.

Ligation of reporter to the fragments was only observed when the correct reporters were available. When during the controls, only one labelled reporter was used with BamH1, Eag1, EcoR1 cut pBR322, then labelled fragments were only observed at scan positions 850 and 1050 of the gel (depending on the actual run) which corresponded to the 375 and 564 base fragments respectively (as judged from the size markers) and only when the TAMRA reporter, (yellow) was present. This corresponded to ligation of the 5'terminal G on the TAMRA reporter to the exposed BamHi cohesive end as expected so that signal could only be observed in the yellow lane.

No significant label was observed in any sample if ligase had not been added during the ligation reactions, confirming that ligation of the reporters was required to label the fragments.

During the first cycle, when all four reporter adaptors were present, significant label was only observed in the TAMRA (yellow) lane at the positions corresponding to the 375 and 564 base fragments. This is again consistent with correct ligation of the terminal G of the TAMRA adaptor to the 375 and 564 base fragments. The other lanes were not significantly labelled at this position—see FIG. 3(a).

One cycle later, the same two fragments are again labelled with TAMRA as expected because a BamH1 cohesive end is GGATCC, so one base further in the 3' direction into the sequence is still on C. An additional fragment at position 1450 corresponding to the 929 Bsa1 to EcoR1 fragment is now also observed to be labelled. This fragment is labelled with FAM (blue) as expected since the C at the 5' end of the FAM reporter should pair with the G exposed four bases in the 3' direction for the 5' end of the Bsa1 generated cohesive end. It is significant that in this case, where three possible ends were available, only the expected reporters found their appropriate ends. Digestion by Bsa1 has abolished the labelling which occurred after the first cycle as expected if this enzyme removes the reporter adaptors. Labelling in the second cycle is not simply as a result of carry over from the first cycle.

Bsa1 digestion after the second and third ligation of reporters also abolishes the labelling as expected if it removes the ligated reporter adaptors. The labelling observed after the third ligation of reporters is also significant because the BamH1 generated ends are observed to be labelled by the JOE reporter (green) which can only arise if a further single base removal occurred during the second Bsa1 cutting and the expected reporter was added during the third reporter ligation. In contrast, a mixture of blue and yellow labelling are observed for the Bsa1 to EcoR1 fragment. This is expected because during the second Bsa1 digestion there are two possible Bsa1 sites that can mutually exclusively be used. The one contributed by the reporter results in removal of the reporter plus one base into the pBR322. The Bsa1 site contributed by the PBR322 results in removal of the reporter but no bases of pBR322 are removed. Two possible ends therefore result at the EcoR1 to Bsa1 generated end. These are differently labelled with either the FAM reporter (C) of the TAMRA reporter (G), depending on the end remaining.

Traces of dye can remain on the fragments after removal of the ligated reporters by Bsa1 . This is expected because restriction endonucleases are not 100% efficient. It does not affect the method because restriction endonucleases at least 95% efficient can be selected so that small amounts of label which remain after digestion can be distinguished from the large amounts of label which are added on ligation of the reporters. The noise contributed by the small number of failures of the restriction enzyme are not expected to be a problem up to at least 20 cycles of the process.

Care has to be exercised during the phenol/chloroform extractions to remove the Bsa1 . More than two phenol/chloroform extractions can be used post-Bsa1 digestion to minimise the Bsa1 "carry over". Alternatively, smaller quantities of enzyme can be used for longer time periods. As yet a further alternative, a more labile enzyme could be used.

In a similar experiment, labelling by the reporters of the small and large Nde1 to Bsa1 fragments of pBR322 were monitored at the Ndel ends through two cycles of cutting and ligation. Samples were cut with Taq1 prior to loading onto the fluorescent gel reader to produce fragments which could be resolved on the gel system used. Oligonucleotides were as described in Example 1.

In this case both the short and large Nde1 to Taq1 fragments were red after the first cycle of ligation of the four reporters, and green after the second cycle of ligation to the reporters. The results are as expected and consistent with only the reporter with the T specific end ligating during the first reporter ligation and the reporter with the A specific end ligating during the second ligation and the base of pBR322 adjacent to the reporter being removed during Bsa1 digestion. Also as expected, the unblocked Bsa1 produced end was blue after one reporter ligation and blue and yellow after the second reporter ligation as discussed above.

Purifying fragments between cycles necessitate using large amounts of starting material to allow for losses occurring during purification. This in turn results in large reaction volumes. This is overcome when fragments are immobilised on a solid phase since then there is no opportunity for the fragments to part from the process. Only sufficient depth of reaction volume to cover the solid phase is required. This can be equivalent to a film of liquid, and therefore reaction volumes (and costs) are lower when a solid phase is used.

What is claimed is:

1. A method of sequencing a double stranded nucleic acid, comprising:

(a) ligating adaptors to said nucleic acid, wherein said adaptors include double stranded oligonucleotide sequence which incorporates a predetermined nuclease recognition sequence for a nuclease whose recognition site is displaced from its cleavage site, said displacement being such as to create, as a result of said litigation, cleavage sites in the resulting ligation products which, upon cleavage thereat, result in removal of a base or bases from one strand of said nucleic acid, and wherein at least some of said adaptors have double stranded oligonucleotide sequence which incorporates at least two different nuclease recognition sequences;

(b) cleaving litigation products from (a) with said nuclease to produce double stranded products having a single stranded oligonucleotide extension;

(c) subjecting said products from (b) to ligation with a population of adaptors which include double stranded oligonucleotide sequence having extending single strands, wherein said population of adaptors includes molecules having in their extending single strands permutations, optionally all possible such permutations, of a base or bases constituting a predetermined number of bases, and wherein each permutation is provided with a respective unique and detectable label, each adaptor in said population having a nuclease recognition sequence for a nuclease whose recognition site is displaced from its cleavage site, said displacement being such as to create, as a result of the ligation of this step (c) cleavage sites in the resulting ligation products which, upon cleavage thereat, result in removal of a base or bases from one strand of each said products from (b);

(d) separating the ligation products from (c);

(e) cleaving the separated ligation products from (d) with the nuclease of (c) to produce a population of fragments carrying the recognition site of nuclease of (c);

(f) either analysing the labels carried by ligation products separated in (d), or analysing the labels carried by fragments from (e); and (g) repeating steps (c) to (f) as often as necessary to determine the desired sequence, but with the final repeat optionally omitting step (e).

2. A method as claimed in claim 1 wherein step (a) is preceded by treatment of said nucleic acid with the nuclease(s) to be used in subsequent steps.

3. A method as claimed in claim 1 wherein the nuclease used in each step (c) is not the same as the nuclease used in step (a).

4. A method as claimed in claim 1 wherein said adaptors are oligonucleotides.

5. A method as claimed in claim 1 wherein said nucleic acids are immobilised.

6. A method as claimed in claim 5, wherein immobilization is achieved using a flat substrate which permits the analysis of step (f) to be performed by scanning, optionally fluorescent scanning.

7. A method as claimed in claim 6, wherein said substrate is a plate or film.

8. A method of sequencing, a double-stranded nucleic acid having a nucleotide sequence comprising sequentially removing nucleotide bases from said nucleotide sequence of the nucleic acid a predetermined number at a time, ligating the product remaining from each step of predetermined nucleotide base removal to a labelled adapter specific for said bases said adaptor including oligonucleotide sequence, containing a predetermined bases(s), the label of said labelled adaptor being specific for its respective predetermined bases(s); wherein at least some of said adaptors have double stranded oligonucleotide sequence which incorporates at least two different nuclease recognition sequences.

9. A method as claimed in claim 8 wherein said adaptors are immobilized.

10. A method as claimed in claim 8 wherein said method proceeds by sequentially removing bases from said nucleic acid being sequenced and before the first step of nucleotide base removal said nucleic acid is subjected to the action of a restriction endonuclease.

11. A method as claimed in claim 8 wherein a population of nucleic acids having nucleotide sequences is sequenced simultaneously.

12. A method as claimed in claim 11 wherein said population of nucleic acids is immobilized.

13. A method of claim 8, wherein sequentially removing nucleotide bases from said nucleic acid having a nucleotide sequence is accomplished by cleaving said nucleic acid ligated to said labeled adaptor with a nuclease having its recognition site displaced from its cleavage site.

* * * * *

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
      (A) LENGTH: 17 bases
      (B) TYPE: nucleotides
      (C) STRANDEDNESS: single (D) TOPOLOGY: linear (xi) SEQUENCE DESCRIPTION: SEQ ID NO: 1:

GAACAGTCCA CCTGTGT                                                          17

(2) INFORMATION FOR SEQ ID NO:2:

(i) SEQUENCE CHARACTERISTICS:
         (A) LENGTH: 21 bases
         (B) TYPE: nucleotides
         (C) STRANDEDNESS: single
         (D) TOPOLOGY: linear (xi) SEQUENCE DESCRIPTION: SEQ ID NO: 2:

ACCGACACAG GTGGACTGTT C                                                     21

(2) INFORMATION FOR SEQ ID NO:3:

(i) SEQUENCE CHARACTERISTICS:
         (A) LENGTH: 28 bases
         (B) TYPE: nucleotides
         (C) STRANDEDNESS: single
         (D) TOPOLOGY: linear (xi) SEQUENCE DESCRIPTION: SEQ ID NO: 3:

TTGACAGGTG CACACGGACG GTCTCCCA                                              28

(2) INFORMATION FOR SEQ ID NO:4:

(i) SEQUENCE CHARACTERISTICS:
         (A) LENGTH: 30 bases
         (B) TYPE: nucleotides
         (C) STRANDEDNESS: single
         (D) TOPOLOGY: linear (xi) SEQUENCE DESCRIPTION: SEQ ID NO: 4:

TATGGGAGAC CGTCCGTGTG CACCTGTCAA                                            30

(2) INFORMATION FOR SEQ ID NO:5:

(i) SEQUENCE CHARACTERISTICS:
         (A) LENGTH: 33 bases
         (B) TYPE: nucleotides
         (C) STRANDEDNESS: single
         (D) TOPOLOGY: linear (xi) SEQUENCE DESCRIPTION: SEQ ID NO: 5:

ANNNGAGACC GAACAGTCCA CCTGTGTCAC TGT                                        33

(2) INFORMATION FOR SEQ ID NO:6:

(i) SEQUENCE CHARACTERISTICS:
         (A) LENGTH: 33 bases
         (B) TYPE: nucleotides
         (C) STRANDEDNESS: single
         (D) TOPOLOGY: linear (xi) SEQUENCE DESCRIPTION: SEQ ID NO: 6:

CNNNGAGACC GAACAGTCCA CCTGTGTCAC TGT                                        33

(2) INFORMATION FOR SEQ ID NO:7:

(i) SEQUENCE CHARACTERISTICS:
         (A) LENGTH: 33 bases
         (B) TYPE: nucleotides
         (C) STRANDEDNESS: single
         (D) TOPOLOGY: linear (xi) SEQUENCE DESCRIPTION: SEQ ID NO: 7:

GNNNGAGACC GAACAGTCCA CCTGTGTCAC TGT         33

(2) INFORMATION FOR SEQ ID NO:8:

(i) SEQUENCE CHARACTERISTICS:
        (A) LENGTH: 33 bases
        (B) TYPE: nucleotides
        (C) STRANDEDNESS: single
        (D) TOPOLOGY: linear (xi) SEQUENCE DESCRIPTION: SEQ ID NO: 8:

TNNNGAGACC GAACAGTCCA CCTGTGTCAC TGT         33

(2) INFORMATION FOR SEQ ID NO:9:

(i) SEQUENCE CHARACTERISTICS:
        (A) LENGTH: 28 bases
        (B) TYPE: nucleotides
        (C) STRANDEDNESS: single
        (D) TOPOLOGY: linear (xi) SEQUENCE DESCRIPTION: SEQ ID NO: 9:

CAGTGACACA GGTGGACTGT TCGGTCTC         28

(2) INFORMATION FOR SEQ ID NO:10:

(i) SEQUENCE CHARACTERISTICS:
        (A) LENGTH: 28 bases
        (B) TYPE: nucleotides
        (C) STRANDEDNESS: single
        (D) TOPOLOGY: linear (xi) SEQUENCE DESCRIPTION: SEQ ID NO: 10:

TTGACAGGTG CACACGGACG GTCTCCCA         28

(2) INFORMATION FOR SEQ ID NO:11:

(i) SEQUENCE CHARACTERISTICS:
        (A) LENGTH: 32 bases
        (B) TYPE: nucleotides
        (C) STRANDEDNESS: single
        (D) TOPOLOGY: linear (xi) SEQUENCE DESCRIPTION: SEQ ID NO: 11:

AATTTGGGAG ACCGTCCGTG TGCACCTGTC AA         32

(2) INFORMATION FOR SEQ ID NO:12:

(i) SEQUENCE CHARACTERISTICS:
        (A) LENGTH: 17 bases
        (B) TYPE: nucleotides
        (C) STRANDEDNESS: single
        (D) TOPOLOGY: linear (xi) SEQUENCE DESCRIPTION: SEQ ID NO: 12:

GAACAGTCCA CCTGTGT         17

(2) INFORMATION FOR SEQ ID NO:13:

(i) SEQUENCE CHARACTERISTICS:
        (A) LENGTH: 21 bases
        (B) TYPE: nucleotides
        (C) STRANDEDNESS: single
        (D) TOPOLOGY: linear (xi) SEQUENCE DESCRIPTION: SEQ ID NO: 13:

GATCACACAG GTGGACTGTT C                                           21

(2) INFORMATION FOR SEQ ID NO:14:

(i) SEQUENCE CHARACTERISTICS:
        (A) LENGTH: 17 bases
        (B) TYPE: nucleotides
        (C) STRANDEDNESS: single
        (D) TOPOLOGY: linear (xi) SEQUENCE DESCRIPTION: SEQ ID NO: 14:

GTAAAACGAC GGCCAGT                                                17

(2) INFORMATION FOR SEQ ID NO:15:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 15:

AANNNNCACC TAATACCCTA TATATA                                      26

(2) INFORMATION FOR SEQ ID NO:16:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 16:

CANNNNCTCA CTAAATCTTA TCTTAC                                      26

(2) INFORMATION FOR SEQ ID NO:17:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 17:

GANNNNCCAA CCCTACATTA ACTTCT                                      26

(2) INFORMATION FOR SEQ ID NO:18:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 18:

TANNNNCAAC ACCCATCCAC TAAACT                                      26

(2) INFORMATION FOR SEQ ID NO:19:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 19:

ACNNNNCACA TAACTCAAAT CACAAA                                              26

(2) INFORMATION FOR SEQ ID NO:20:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 20:

CCNNNNCTAA CAACAAACCT TACTAC                                              26

(2) INFORMATION FOR SEQ ID NO:21:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 21:

GCNNNNCCCT TCTACCAACC TATATC                                              26

(2) INFORMATION FOR SEQ ID NO:22:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 22:

TCNNNNCCTT ACACTTTATC ACACCC                                              26

(2) INFORMATION FOR SEQ ID NO:23:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 23:

AGNNNNCAAA AACTAATTCC CAAAAA                                              26

(2) INFORMATION FOR SEQ ID NO:24:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 24:

CGNNNNCAAC CACAACCAAC CCTACT                                              26

(2) INFORMATION FOR SEQ ID NO:25:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 25:

GGNNNNCCTA ATCATCAATA TACTCA                                                26

(2) INFORMATION FOR SEQ ID NO:26:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 26:

TGNNNNCAAA CCAACATTTA ACACAA                                                26

(2) INFORMATION FOR SEQ ID NO:27:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 27:

ATNNNNCAAC CAACTCTACT TATCAC                                                26

(2) INFORMATION FOR SEQ ID NO:28:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 28:

CTNNNNCAAT ATTTAAACCT CACACT                                                26

(2) INFORMATION FOR SEQ ID NO:29:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 29:

GTNNNNCATA ATATAACCTA AACCCT                                                26

(2) INFORMATION FOR SEQ ID NO:30:

(i) SEQUENCE CHARACTERISTICS:
        (A) LENGTH: 26 bases
        (B) TYPE: nucleotides
        (C) STRANDEDNESS: single
        (D) TOPOLOGY: linear (xi) SEQUENCE DESCRIPTION: SEQ ID NO: 30:

TTNNNNGTAA GGTGGTGTAA AAGGAA                                                26

(2) INFORMATION FOR SEQ ID NO:31:

(i) SEQUENCE CHARACTERISTICS:
        (A) LENGTH: 17 bases
        (B) TYPE: nucleotides
        (C) STRANDEDNESS: single
        (D) TOPOLOGY: linear (xi) SEQUENCE DESCRIPTION: SEQ ID NO: 31:

AATTCGGAGT GAAAGCG                                                          17

(2) INFORMATION FOR SEQ ID NO:32:

(i) SEQUENCE CHARACTERISTICS:
        (A) LENGTH: 12 bases
        (B) TYPE: nucleotides
        (C) STRANDEDNESS: single
        (D) TOPOLOGY: linear (xi) SEQUENCE DESCRIPTION: SEQ ID NO: 32:

GCTTTCACTC CG                                                          12

(2) INFORMATION FOR SEQ ID NO:33:

(i) SEQUENCE CHARACTERISTICS:
        (A) LENGTH: 15 bases
        (B) TYPE: nucleotides
        (C) STRANDEDNESS: single
        (D) TOPOLOGY: linear (xi) SEQUENCE DESCRIPTION: SEQ ID NO: 33:

GGCCGGCCTG ACTCT                                                       15

(2) INFORMATION FOR SEQ ID NO:34:

(i) SEQUENCE CHARACTERISTICS:
        (A) LENGTH: 12 bases
        (B) TYPE: nucleotides
        (C) STRANDEDNESS: single
        (D) TOPOLOGY: linear (xi) SEQUENCE DESCRIPTION: SEQ ID NO: 34:

GAGAGTCAGG CC                                                          12

(2) INFORMATION FOR SEQ ID NO:35:

(i) SEQUENCE CHARACTERISTICS:
        (A) LENGTH: 12 bases
        (B) TYPE: nucleotides
        (C) STRANDEDNESS: single
        (D) TOPOLOGY: linear (xi) SEQUENCE DESCRIPTION: SEQ ID NO: 35:

GCCAAGCTTG CA                                                          12

(2) INFORMATION FOR SEQ ID NO:36:

(i) SEQUENCE CHARACTERISTICS:
        (A) LENGTH: 18 bases
        (B) TYPE: nucleotides
        (C) STRANDEDNESS: single
        (D) TOPOLOGY: linear (xi) SEQUENCE DESCRIPTION: SEQ ID NO: 36:

ACGTTACGNN NNGAGACC                                                    18

(2) INFORMATION FOR SEQ ID NO:37:

(i) SEQUENCE CHARACTERISTICS:
        (A) LENGTH: 18 bases
        (B) TYPE: nucleotides
        (C) STRANDEDNESS: single
        (D) TOPOLOGY: linear (xi) SEQUENCE DESCRIPTION: SEQ ID NO: 37:

GGTCTCNNNN CGTAACGT                                                    18

(2) INFORMATION FOR SEQ ID NO:38:

(i) SEQUENCE CHARACTERISTICS:
        (A) LENGTH: 18 bases
        (B) TYPE: nucleotides
        (C) STRANDEDNESS: single
        (D) TOPOLOGY: linear (xi) SEQUENCE DESCRIPTION: SEQ ID NO: 38:

TGCACGATNN NNGAGACC    18

(2) INFORMATION FOR SEQ ID NO:39:

(i) SEQUENCE CHARACTERISTICS:
        (A) LENGTH: 18 bases
        (B) TYPE: nucleotides
        (C) STRANDEDNESS: single
        (D) TOPOLOGY: linear (xi) SEQUENCE DESCRIPTION: SEQ ID NO: 39:

GGTCTCNNNN ATCGTGCA    18

(2) INFORMATION FOR SEQ ID NO:40:

(i) SEQUENCE CHARACTERISTICS:
        (A) LENGTH: 23 bases
        (B) TYPE: nucleotides
        (C) STRANDEDNESS: single
        (D) TOPOLOGY: linear (xi) SEQUENCE DESCRIPTION: SEQ ID NO: 40:

AAGCTAGGCT CCGGATGACG GGA    23